(12) United States Patent
Zamir et al.

(10) Patent No.: US 7,897,840 B2
(45) Date of Patent: Mar. 1, 2011

(54) SALT RESPONSIVE GENES USEFUL FOR GENERATING SALT RESISTANT TRANSGENIC PLANTS

(75) Inventors: Ada Zamir, Rehovot (IL); Irena Gokhman, Rehovot (IL); Eli Khayat, Western Galilee (IL); Nataly Vinikur, Nahariya (IL); Orna Livneh, Rehovot (IL); Avi Gabai, Vardon (IL)

(73) Assignees: Hazera Genetics Ltd., Shikim (IL); Rahan Meristem (1998) Ltd., Rosh Hanikra (IL); Yeda Research and Development Co., Ltd. at The Weizmann Institute of Science, Rehovot (IL)

( * ) Notice: Subject to any disclaimer, the term of this patent is extended or adjusted under 35 U.S.C. 154(b) by 615 days.

(21) Appl. No.: 11/574,507

(22) PCT Filed: Sep. 1, 2005

(86) PCT No.: PCT/IL2005/000933
§ 371 (c)(1),
(2), (4) Date: Jul. 6, 2007

(87) PCT Pub. No.: WO2006/025060
PCT Pub. Date: Mar. 9, 2006

(65) Prior Publication Data
US 2009/0217411 A1 Aug. 27, 2009

Related U.S. Application Data

(60) Provisional application No. 60/606,414, filed on Sep. 2, 2004.

(51) Int. Cl.
*A01H 5/00* (2006.01)
*C12N 15/82* (2006.01)
*C12N 5/14* (2006.01)
*C07H 21/00* (2006.01)

(52) U.S. Cl. ......... 800/295; 800/278; 800/298; 435/419; 435/468; 536/23.6

(58) Field of Classification Search .................. None
See application file for complete search history.

(56) References Cited

U.S. PATENT DOCUMENTS

2002/0160378 A1  10/2002  Harper et al. ............... 435/6

OTHER PUBLICATIONS

Yamada et al. (NCBI, GenBank Sequence Accession No. AY065228, Published Sep. 18, 2002).*
International Search Report for PCT/IL2005/000933 dated Apr. 8, 2008 (6 pages).
Written Opinion of the International Searching Authority for PCT/IL2005/000933 dated Apr. 8, 2008 (7 pages).

* cited by examiner

*Primary Examiner* — Vinod Kumar
(74) *Attorney, Agent, or Firm* — KK Patents, LLC; Lyn Marantz

(57) ABSTRACT

The present invention provides transgenic plants transformed with exogenous nucleic acid encoding a *Dunaliella* salt-inducible or salt-responsive protein selected from the group consisting of eukaryotic initiation factor 3 (eIF3) subunit, NADPH dependent quinone reductase (QOR), aldo-keto reductase (AKR), bifunctional aspartate kinase-homoserine reductase (AK-HSD) and mitochondrial import membrane translocase subunit (TIM9), or a fragment, homolog or variant thereof. The transgenic plants have increased tolerance to salt as compared to corresponding non-transgenic plants. The present invention further provides nucleic acids, constructs and vectors encoding the *Dunaliella* salt-inducible or otherwise salt-responsive proteins, and to a method of producing transgenic plants having an increased tolerance to salt, a method of modifying plant capacity to survive salt shock, and a method of modifying plant recovery after exposure to salt stress, by introducing the nucleic acids, constructs and/or vectors into one or more cells of the plant.

28 Claims, 18 Drawing Sheets

```
    ATGAGGCCTTACCTGCTCAAGGGCCATGATAGACCCCTTACCCAAGTAAAGTTCAACCGC
1   ---------+---------+---------+---------+---------+---------+
    TACTCCGGAATGGACGAGTTCCCGGTACTATCTGGGGAATGGGTTCATTTCAAGTTGGCG
    M  R  P  Y  L  L  K  G  H  D  R  P  L  T  Q  V  K  F  N  R
    GAGGGAGACCTTTTCGTGACCTGTGCCAAGAACAACCAGTCATGCCTGTGGTGGTCAGAT
61  ---------+---------+---------+---------+---------+---------+
    CTCCCTCTGGAAAAGCACTGGACACGGTTCTTGTTGGTCAGTACGGACACCACCAGTCTA
    E  G  D  L  F  V  T  C  A  K  N  N  Q  S  C  L  W  W  S  D
    GATGGAAAGCGTGTGGGCACCTTTGAGGGTCACAATGGTGCTGTGTGGAGCTGCGACATG
121 ---------+---------+---------+---------+---------+---------+
    CTACCTTTCGCACACCCGTGGAAACTCCCAGTGTTACCACGACACACCTCGACGCTGTAC
    D  G  K  R  V  G  T  F  E  G  H  N  G  A  V  W  S  C  D  M
    ACATGGGAGTCTGACCGGCTCATCACCGCCTCTGCCGACCAGACAGTCCGGATATGGAC
181 ---------+---------+---------+---------+---------+---------+
    TGTACCCTCAGACTGGCCGAGTAGTGGCGGAGACGGCTGGTCTGTCAGGCCTATACCCTG
    T  W  E  S  D  R  L  I  T  A  S  A  D  Q  T  V  R  I  W  D
    ATGACCAATGGCAAGGAGCAGTTCCAGTTCAAGATGGGGGAGCCATGCCGCGCATGCAAC
241 ---------+---------+---------+---------+---------+---------+
    TACTGGTTACCGTTCCTCGTCAAGGTCAAGTTCTACCCCCTCGGTACGGCGCGTACGTTG
    M  T  N  G  K  E  Q  F  Q  F  K  M  G  E  P  C  R  A  C  N
    CTCAGCTTGGGGGAGCAGATGCTTGCCTTCACCACTGACGCTTTCATGGGCAGCTCCCCC
301 ---------+---------+---------+---------+---------+---------+
    GAGTCGAACCCCCTCGTCTACGAACGGAAGTGGTGACTGCGAAAGTACCCGTCGAGGGGG
    L  S  L  G  E  Q  M  L  A  F  T  T  D  A  F  M  G  S  S  P
    ATGGTTCACTTGGCTAAGCTGGAAGACGACCTCTCCCAACAAACTACCAAGACTGTGCTC
361 ---------+---------+---------+---------+---------+---------+
    TACCAAGTGAACCGATTCGACCTTCTGCTGGAGAGGGTTGTTTGATGGTTCTGACACGAG
    M  V  H  L  A  K  L  E  D  D  L  S  Q  Q  T  T  K  T  V  L
    GGCATACAAGCTCCTAAGGGCCGCATTACGCGGGTGTTCTGGTCAGATATGAACCGCACA
421 ---------+---------+---------+---------+---------+---------+
    CCGTATGTTCGAGGATTCCCGGCGTAATGCGCCCACAAGACCAGTCTATACTTGGCGTGT
    G  I  Q  A  P  K  G  R  I  T  R  V  F  W  S  D  M  N  R  T
    CTAGTGACCTCGCATGATGGTGGATTCATGCGCAAGTGGGATTCAGAGACCGGGAAGATG
481 ---------+---------+---------+---------+---------+---------+
    GATCACTGGAGCGTACTACCACCTAAGTACGCGTTCACCCTAAGTCTCTGGCCCTTCTAC
    L  V  T  S  H  D  G  G  F  M  R  K  W  D  S  E  T  G  K  M
    CTGTTAGAGAAGCAAGTGCATGAGGGCGACATCCAAGACATGCAGATGTCCCCCGATGGT
541 ---------+---------+---------+---------+---------+---------+
    GACAATCTCTTCGTTCACGTACTCCCGCTGTAGGTTCTGTACGTCTACAGGGGGCTACCA
    L  L  E  K  Q  V  H  E  G  D  I  Q  D  M  Q  M  S  P  D  G
```

FIG. 1i

```
     GCCTACTTCATCACAGCCTCCTTAGACAAAACTGCCAAGCTCGTGGACGCTGTGGAGCTT
601  ----------+---------+---------+---------+---------+---------+
     CGGATGAAGTAGTGTCGGAGGAATCTGTTTTGACGGTTCGAGCACCTGCGACACCTCGAA
      A  Y  F  I  T  A  S  L  D  K  T  A  K  L  V  D  A  V  E  L

GAAGCCTTGAAGACGTACAAGACTGGGCGCTTTGTACAATCTGCAGCCATTTCACCGCTG
661  ----------+---------+---------+---------+---------+---------+
     CTTCGGAACTTCTGCATGTTCTGACCCGCGAAACATGTTAGACGTCGGTAAAGTGGCGAC
      E  A  L  K  T  Y  K  T  G  R  F  V  Q  S  A  A  I  S  P  L

TTTGACCATGTATTGCTGGGGGGAGGTCAGGATGCTTCTCAAGTGACAACGACCTCCTCT
721  ----------+---------+---------+---------+---------+---------+
     AAACTGGTACATAACGACCCCCCTCCAGTCCTACGAAGAGTTCACTGTTGCTGGAGGAGA
      F  D  H  V  L  L  G  G  G  Q  D  A  S  Q  V  T  T  T  S  S

AAGGCTGGCGGTTTTGAGGCGCGCTTCTTTCACAAGATTTACCAGGAAGAATTTGGAAAC
781  ----------+---------+---------+---------+---------+---------+
     TTCCGACCGCCAAAACTCCGCGCGAAGAAAGTGTTCTAAATGGTCCTTCTTAAACCTTTG
      K  A  G  G  F  E  A  R  F  F  H  K  I  Y  Q  E  E  F  G  N

GTAAGAGGGCATTTCGGACCTATCAACACTGTGGCATTCCATCCGAGTGGAAAAAGCTTC
841  ----------+---------+---------+---------+---------+---------+
     CATTCTCCCGTAAAGCCTGGATAGTTGTGACACCGTAAGGTAGGCTCACCTTTTTCGAAG
      V  R  G  H  F  G  P  I  N  T  V  A  F  H  P  S  G  K  S  F

TTGACAGGTGGAGAGGATGGATATGTGCGCTTGCACCATTTTGACCTCGATTACTTCACC
901  ----------+---------+---------+---------+---------+---------+
     AACTGTCCACCTCTCCTACCTATACACGCGAACGTGGTAAAACTGGAGCTAATGAAGTGG
      L  T  G  G  E  D  G  Y  V  R  L  H  H  F  D  L  D  Y  F  T

ACGAAATTCTTCTGA
961  ----------+----- 975
     TGCTTTAAGAAGACT
      T  K  F  F  *
```

FIG. 1ii

```
     ATGGCTTGCAAGGCTCAGACGGTGCTGTTCAAGGAGTACGTGGAGGTCGGCGAGGTCCCA
  1  ---------+---------+---------+---------+---------+---------+
     TACCGAACGTTCCGAGTCTGCCACGACAAGTTCCTCATGCACCTCCAGCCGCTCCAGGGT
     M  A  C  K  A  Q  T  V  L  F  K  E  Y  V  E  V  G  E  V  P

CCTGACAACTTCCAGCTAAGGACAATCGATCTACCCGCCCTGAAGGATGGCGAGGTCCTT
 61  ---------+---------+---------+---------+---------+---------+
     GGACTGTTGAAGGTCGATTCCTGTTAGCTAGATGGGCGGGACTTCCTACCGCTCCAGGAA
     P  D  N  F  Q  L  R  T  I  D  L  P  A  L  K  D  G  E  V  L

CTTGAGCTGCAGTACCTGAGTGTGGATCCTTACATGCGTGGCCGCATGCGCAATGCAGCA
121  ---------+---------+---------+---------+---------+---------+
     GAACTCGACGTCATGGACTCACACCTAGGAATGTACGCACCGGCGTACGCGTTACGTCGT
     L  E  L  Q  Y  L  S  V  D  P  Y  M  R  G  R  M  R  N  A  A

GGCTACTTTGTTGGGCCCTTTGTGCCAGGCGAGGCCCTCAGTGGAGGTGGAGTTGTAGTT
181  ---------+---------+---------+---------+---------+---------+
     CCGATGAAACAACCCGGGAAACACGGTCCGCTCCGGGAGTCACCTCCACCTCAACATCAA
     G  Y  F  V  G  P  F  V  P  G  E  A  L  S  G  G  G  V  V  V

GTCAAGGAGAGCAAGGCTCCCGGCATTGAGAAGGGCAAGTTCTACAGTGGCATGGTCCCC
241  ---------+---------+---------+---------+---------+---------+
     CAGTTCCTCTCGTTCCGAGGGCCGTAACTCTTCCCGTTCAAGATGTCACCGTACCAGGGG
     V  K  E  S  K  A  P  G  I  E  K  G  K  F  Y  S  G  M  V  P

TGGACTTCCCCTCAAATCGCAACCAAGGCACAGATGGAGCAGATGCAGCCTGTAGACACT
301  ---------+---------+---------+---------+---------+---------+
     ACCTGAAGGGGAGTTTAGCGTTGGTTCCGTGTCTACCTCGTCTACGTCGGACATCTGTGA
     W  T  S  P  Q  I  A  T  K  A  Q  M  E  Q  M  Q  P  V  D  T

GACATCCTCAAGTTGGCTAAGCTGCCCCTGTCCGGATACGCTGGTGTGTTCGGCCTGACG
361  ---------+---------+---------+---------+---------+---------+
     CTGTAGGAGTTCAACCGATTCGACGGGGACAGGCCTATGCGACCACACAAGCCGGACTGC
     D  I  L  K  L  A  K  L  P  L  S  G  Y  A  G  V  F  G  L  T

GGCATGACAGCGTATGCCTCACTCACCAGGATTGGCAAGCCAAAGAAGGGAGAGACTGTG
421  ---------+---------+---------+---------+---------+---------+
     CCGTACTGTCGCATACGGAGTGAGTGGTCCTAACCGTTCGGTTTCTTCCCTCTCTGACAC
     G  M  T  A  Y  A  S  L  T  R  I  G  K  P  K  K  G  E  T  V

TTTGTCTCGGGTGCTGCTGGGGCTGTTGGCATGATTGTGGGCCAGATGTGCAAGAATGTG
481  ---------+---------+---------+---------+---------+---------+
     AAACAGAGCCCACGACGACCCCGACAACCGTACTAACACCCGGTCTACACGTTCTTACAC
     F  V  S  G  A  A  G  A  V  G  M  I  V  G  Q  M  C  K  N  V

TACGGATGCAAGGTGGTTGGCTCTGCGGGAAGTGAGGACAAGGTGGAGTTCCTGACAAAG
541  ---------+---------+---------+---------+---------+---------+
     ATGCCTACGTTCCACCAACCGAGACGCCCTTCACTCCTGTTCCACCTCAAGGACTGTTTC
     Y  G  C  K  V  V  G  S  A  G  S  E  D  K  V  E  F  L  T  K
```

FIG. 2i

```
      GAGTTGGGCTTCGACGCGGCTTGGAACTACAAGACAATGCCCACCTTGGATGCTTTGAAC
601   ---------+---------+---------+---------+---------+---------+
      CTCAACCCGAAGCTGCGCCGAACCTTGATGTTCTGTTACGGGTGGAACCTACGAAACTTG
       E  L  G  F  D  A  A  W  N  Y  K  T  M  P  T  L  D  A  L  N
      AAGTTCTGCCCTGAAGGCATTGACATGTACTACGAGAATGTTGGCGGTGAGCAGCTAGAG
661   ---------+---------+---------+---------+---------+---------+
      TTCAAGACGGGACTTCCGTAACTGTACATGATGCTCTTACAACCGCCACTCGTCGATCTC
       K  F  C  P  E  G  I  D  M  Y  Y  E  N  V  G  G  E  Q  L  E
      GCCGCACTCGAAAAGTGCAGGGAAAATGCACGCATTGTGTGCTGCGGTATGATCTCACAA
721   ---------+---------+---------+---------+---------+---------+
      CGGCGTGAGCTTTTCACGTCCCTTTTACGTGCGTAACACACGACGCCATACTAGAGTGTT
       A  A  L  E  K  C  R  E  N  A  R  I  V  C  C  G  M  I  S  Q
      TACAACAAGAAGGGAGATGACCGCTATGGCGTGAAGAACTTGGCGAACGTGGTGTTCAAG
781   ---------+---------+---------+---------+---------+---------+
      ATGTTGTTCTTCCCTCTACTGGCGATACCGCACTTCTTGAACCGCTTGCACCACAAGTTC
       Y  N  K  K  G  D  D  R  Y  G  V  K  N  L  A  N  V  V  F  K
      AAGATCAAGATGGAGGGCTTCTTGCTGTTCCAATTCCTGCCTGAGGTTGTTCCTGAATTC
841   ---------+---------+---------+---------+---------+---------+
      TTCTAGTTCTACCTCCCGAAGAACGACAAGGTTAAGGACGGACTCCAACAAGGACTTAAG
       K  I  K  M  E  G  F  L  L  F  Q  F  L  P  E  V  V  P  E  F
      TTTGAGCACTTCCCCAAGTGGATAGCTGAGGGCAAGATCAAGGACACAGAGTACGTTGTC
901   ---------+---------+---------+---------+---------+---------+
      AAACTCGTGAAGGGGTTCACCTATCGACTCCCGTTCTAGTTCCTGTGTCTCATGCAACAG
       F  E  H  F  P  K  W  I  A  E  G  K  I  K  D  T  E  Y  V  V
      AAAGGCGGCTTGGCGAATGCTGGCCAGGCTTTCTGCGACATGATGGCCGGAAAGAACAAG
961   ---------+---------+---------+---------+---------+---------+
      TTTCCGCCGAACCGCTTACGACCGGTCCGAAAGACGCTGTACTACCGGCCTTTCTTGTTC
       K  G  G  L  A  N  A  G  Q  A  F  C  D  M  M  A  G  K  N  K
      GGCAAGGCTGTGGTGAAGTGCGTGGACAAGGACCCTATTGTGGGGAACTAA
1021  ---------+---------+---------+---------+---------+-
      CCGTTCCGACACCACTTCACGCACCTGTTCCTGGGATAACACCCCTTGATT
       G  K  A  V  V  K  C  V  D  K  D  P  I  V  G  N  *
```

FIG. 2ii

```
     ATGTCTACCGCCAATGTGCAGGTGCAGCAGGGTGACAAGCCCCAGCCCGTGAAGACCGGC
  1  ---------+---------+---------+---------+---------+---------+
     TACAGATGGCGGTTACACGTCCACGTCGTCCCACTGTTCGGGGTCGGGCACTTCTGGCCG
      M  S  T  A  N  V  Q  V  Q  Q  G  D  K  P  Q  P  V  K  T  G
     AACACCAATGAGCCTGACTACGTGAGGCTGTCCAACGGCGTGCTCATGCCCTTGATTGGC
 61  ---------+---------+---------+---------+---------+---------+
     TTGTGGTTACTCGGACTGATGCACTCCGACAGGTTGCCGCACGAGTACGGGAACTAACCG
      N  T  N  E  P  D  Y  V  R  L  S  N  G  V  L  M  P  L  I  G
     TACGGCACCTTCCAGCTGCAAGATGCAGACATGGTCAAGCAAGCTTTGGAGGTGGGCTAC
121  ---------+---------+---------+---------+---------+---------+
     ATGCCGTGGAAGGTCGACGTTCTACGTCTGTACCAGTTCGTTCGAAACCTCCACCCGATG
      Y  G  T  F  Q  L  Q  D  A  D  M  V  K  Q  A  L  E  V  G  Y
     CGCCACTTAGACTGTGCCTCCCTGTATGGCAACCAGGAGCTCGTCGGCAGGGGCATTGCC
181  ---------+---------+---------+---------+---------+---------+
     GCGGTGAATCTGACACGGAGGGACATACCGTTGGTCCTCGAGCAGCCGTCCCCGTAACGG
      R  H  L  D  C  A  S  L  Y  G  N  Q  E  L  V  G  R  G  I  A
     AGCTGGATTGCTGCAGACCCCAGCAAGAACAAGCGCGAGGACCTGTTTGTGACCAGCAAG
241  ---------+---------+---------+---------+---------+---------+
     TCGACCTAACGACGTCTGGGGTCGTTCTTGTTCGCGCTCCTGGACAAACACTGGTCGTTC
      S  W  I  A  A  D  P  S  K  N  K  R  E  D  L  F  V  T  S  K
     ATTTTTAATGATGAGCACCGGCCAGAGCTGCTGCGCAAGTCAGCGGAGAAGAGCATTGCT
301  ---------+---------+---------+---------+---------+---------+
     TAAAAATTACTACTCGTGGCCGGTCTCGACGACGCGTTCAGTCGCCTCTTCTCGTAACGA
      I  F  N  D  E  H  R  P  E  L  L  R  K  S  A  E  K  S  I  A
     GAGCTAGGGACCAAGTACCTGGACCTGCTGCTGCTGCACTGGCCCAATGCCTTCAAGCCT
361  ---------+---------+---------+---------+---------+---------+
     CTCGATCCCTGGTTCATGGACCTGGACGACGACGACGTGACCGGGTTACGGAAGTTCGGA
      E  L  G  T  K  Y  L  D  L  L  L  L  H  W  P  N  A  F  K  P
     GGATCAGGCAGCTCCTTCCATGGTGACGTGTGCCCAGCAGAGGGCGAGAAGCCCCCTGGA
421  ---------+---------+---------+---------+---------+---------+
     CCTAGTCCGTCGAGGAAGGTACCACTGCACACGGGTCGTCTCCCGCTCTTCGGGGGACCT
      G  S  G  S  S  F  H  G  D  V  C  P  A  E  G  E  K  P  P  G
     TGCGTCGTGTTTGATGATGAGGTCACCCACGAGCAGACCTGGCGCGCCATGGAGAAGCTG
481  ---------+---------+---------+---------+---------+---------+
     ACGCAGCACAAACTACTACTCCAGTGGGTGCTCGTCTGGACCGCGCGGTACCTCTTCGAC
      C  V  V  F  D  D  E  V  T  H  E  Q  T  W  R  A  M  E  K  L
```

FIG. 3i

```
                GTGGACGATGGTCTGGTGCGATGCATTGGCCTGTCCAACTTCAGCCACAAGGAGGTGACC
       541      ---------+---------+---------+---------+---------+---------+
                CACCTGCTACCAGACCACGCTACGTAACCGGACAGGTTGAAGTCGGTGTTCCTCCACTGG
                 V  D  D  G  L  V  R  C  I  G  L  S  N  F  S  H  K  E  V  T
                CACATCTGCAATATTGCCAGGATCAAGCCTACCATCAACGAGATTGAGCTACACCCCTTC
       601      ---------+---------+---------+---------+---------+---------+
                GTGTAGACGTTATAACGGTCCTAGTTCGGATGGTAGTTGCTCTAACTCGATGTGGGGAAG
                 H  I  C  N  I  A  R  I  K  P  T  I  N  E  I  E  L  H  P  F
                CTGGCACAGAAGGAGTTTGTGGCTTGGTGCGCGAGCATGGGAGTGACCTGCCTGGCATAC
       661      ---------+---------+---------+---------+---------+---------+
                GACCGTGTCTTCCTCAAACACCGAACCACGCGCTCGTACCCTCACTGGACGGACCGTATG
                 L  A  Q  K  E  F  V  A  W  C  A  S  M  G  V  T  C  L  A  Y
                GGTCCCCTCGGCGGCCCCAACGCTTACCTCCCCAACGACCTGCTGCCCCACCCCACCGTC
       721      ---------+---------+---------+---------+---------+---------+
                CCAGGGGAGCCGCCGGGGTTGCGAATGGAGGGGTTGCTGGACGACGGGGTGGGGTGGCAG
                 G  P  L  G  G  P  N  A  Y  L  P  N  D  L  L  P  H  P  T  V
                ACCAAGGTTGCTCAGGAGGCCGGCAAGACCAACGGCCGGATCCTGGTGAAGTGGAGCGTC
       781      ---------+---------+---------+---------+---------+---------+
                TGGTTCCAACGAGTCCTCCGGCCGTTCTGGTTGCCGGCCTAGGACCACTTCACCTCGCAG
                 T  K  V  A  Q  E  A  G  K  T  N  G  R  I  L  V  K  W  S  V
                CAGCGCGGCGTGCCTGTCCTGGTGAAGACCGGCACTGCCTCTCGCCTGAAGGAGAACCTG
       841      ---------+---------+---------+---------+---------+---------+
                GTCGCGCCGCACGGACAGGACCACTTCTGGCCGTGACGGAGAGCGGACTTCCTCTTGGAC
                 Q  R  G  V  P  V  L  V  K  T  G  T  A  S  R  L  K  E  N  L
                TGGGGCATGATGGACTACAAGCTGACCGACGAGCAGATGGCGGCTCTAGACTCTTTGGAA
       901      ---------+---------+---------+---------+---------+---------+
                ACCCCGTACTACCTGATGTTCGACTGGCTGCTCGTCTACCGCCGAGATCTGAGAAACCTT
                 W  G  M  M  D  Y  K  L  T  D  E  Q  M  A  A  L  D  S  L  E
                AACGGCAAGCGGCTTGTGACTGTCCCGTGGAAGAAGTGGGAGACTGAGCCCGTTCCTGAC
       961      ---------+---------+---------+---------+---------+---------+
                TTGCCGTTCGCCGAACACTGACAGGGCACCTTCTTCACCCTCTGACTCGGGCAAGGACTG
                 N  G  K  R  L  V  T  V  P  W  K  K  W  E  T  E  P  V  P  D
                CCTGTCCCTTCCACGAAGGCTTGA
      1021      ---------+---------+----  1044
                GGACAGGGAAGGTGCTTCCGAACT
                 P  V  P  S  T  K  A  *
```

FIG. 3ii

```
      ATGCTTCTGCGGGCCAATTGTGCTGCAGGGCTGGGATGCAAAGCGTCTTCCGGAAAGACG
  1   ---------+---------+---------+---------+---------+---------+
      TACGAAGACGCCCGGTTAACACGACGTCCCGACCCTACGTTTCGCAGAAGGCCTTTCTGC
      M  L  L  R  A  N  C  A  A  G  L  G  C  K  A  S  S  G  K  T
      CCTGCAGCTGCTCCCGCAAATGTCGCTGGTTTCACCGCGCAGCACTCTGCCTGCTTCGGA
 61   ---------+---------+---------+---------+---------+---------+
      GGACGTCGACGAGGGCGTTTACAGCGACCAAAGTGGCGCGTCGTGAGACGGACGAAGCCT
      P  A  A  A  P  A  N  V  A  G  F  T  A  Q  H  S  A  C  F  G
      AAGGCGTCCAGCTCCACCCGTAATCATCATCATGTCATCACCCCGCTCCTCCCCTCGTGC
121   ---------+---------+---------+---------+---------+---------+
      TTCCGCAGGTCGAGGTGGGCATTAGTAGTAGTACAGTAGTGGGGCGAGGAGGGGAGCACG
      K  A  S  S  S  T  R  N  H  H  H  V  I  T  P  L  L  P  S  C
      CCAGCTCCCCTCATGCCCCAAGCAGCCCACAGCAGCGCCATCTGCCGAGCAGTAGTTGCC
181   ---------+---------+---------+---------+---------+---------+
      GGTCGAGGGGAGTACGGGGTTCGTCGGGTGTCGTCGCGGTAGACGGCTCGTCATCAACGG
      P  A  P  L  M  P  Q  A  A  H  S  S  A  I  C  R  A  V  V  A
      CCTGTGGAGACGGAGGCAGGGGGTGCCCCCTTTCAGCGCGGTTCCGGCTGGGCGCTGCAC
241   ---------+---------+---------+---------+---------+---------+
      GGACACCTCTGCCTCCGTCCCCCACGGGGGAAAGTCGCGCCAAGGCCGACCCGCGACGTG
      P  V  E  T  E  A  G  A  P  F  Q  R  G  S  G  W  A  L  H
      AAGTTTGGCGGCACTTGCATGGCCGCTGCTGAGCGCATTGCCGGGGCAAGCAAGCTGATG
301   ---------+---------+---------+---------+---------+---------+
      TTCAAACCGCCGTGAACGTACCGGCGACGACTCGCGTAACGGCCCCGTTCGTTCGACTAC
      K  F  G  G  T  C  M  A  A  A  E  R  I  A  G  A  S  K  L  M
      ATTGACATCAACCCTGATGCAGAGGGAAAGGTGGCCGTTGTGAGCGCGATGGGCTCACAC
361   ---------+---------+---------+---------+---------+---------+
      TAACTGTAGTTGGGACTACGTCTCCCTTTCCACCGGCAACACTCGCGCTACCCGAGTGTG
      I  D  I  N  P  D  A  E  G  K  V  A  V  V  S  A  M  G  S  H
      CCGACTTCGCCCCTGAAGGTGACAGACGTGATCCTCCAGATGATCGCCAAGGCTGAGCGC
421   ---------+---------+---------+---------+---------+---------+
      GGCTGAAGCGGGGACTTCCACTGTCTGCACTAGGAGGTCTACTAGCGGTTCCGACTCGCG
      P  T  S  P  L  K  V  T  D  V  I  L  Q  M  I  A  K  A  E  R
      CAGGACCAGCGCTTCCTGCTAGACCTGGCCGCACCGCAAGATAAGCACGTTGACTCCGCC
481   ---------+---------+---------+---------+---------+---------+
      GTCCTGGTCGCGAAGGACGATCTGGACCGGCGTGGCGTTCTATTCGTGCAACTGAGGCGG
      Q  D  Q  R  F  L  L  D  L  A  A  P  Q  D  K  H  V  D  S  A
      AAGGAGCTGCTGGGCGAGAGCAAGGAGCTGACCTACTTTGTGGGCCGCTTGCTAGAGGAC
541   ---------+---------+---------+---------+---------+---------+
      TTCCTCGACGACCCGCTCTCGTTCCTCGACTGGATGAAACACCCGGCGAACGATCTCCTG
      K  E  L  L  G  E  S  K  E  L  T  Y  F  V  G  R  L  L  E  D
```

FIG. 4i

```
     ATCAACAACCTGAAGGCGATGCTGAACGCCATGAGCATCGCCGGTATGACCACAGAGGCA
601  ---------+---------+---------+---------+---------+---------+
     TAGTTGTTGGACTTCCGCTACGACTTGCGGTACTCGTAGCGGCCATACTGGTGTCTCCGT
      I  N  N  L  K  A  M  L  N  A  M  S  I  A  G  M  T  T  E  A
     TTCTCGGACTATGTGGTGGGCCACGGCGAGCTGTGGAGCGCGCAGCTCATGGCATTGTAC
661  ---------+---------+---------+---------+---------+---------+
     AAGAGCCTGATACACCACCCGGTGCCGCTCGACACCTCGCGCGTCGAGTACCGTAACATG
      F  S  D  Y  V  V  G  H  G  E  L  W  S  A  Q  L  M  A  L  Y
     TGCCAGCAGCTGGGCGCAGACTGTGTCTTCATGGACGCGCGCGATGTGCTGGTTGTGTCC
721  ---------+---------+---------+---------+---------+---------+
     ACGGTCGTCGACCCGCGTCTGACACAGAAGTACCTGCGCGCGCTACACGACCAACACAGG
      C  Q  Q  L  G  A  D  C  V  F  M  D  A  R  D  V  L  V  V  S
     CCCACTAGCGATGGCACCAGCGTGGATTTGGTGGAGGATGCGTCCAACGCGCGCTTGGAC
781  ---------+---------+---------+---------+---------+---------+
     GGGTGATCGCTACCGTGGTCGCACCTAAACCACCTCCTACGCAGGTTGCGCGCGAACCTG
      P  T  S  D  G  T  S  V  D  L  V  E  D  A  S  N  A  R  L  D
     GCATGGTTCCGGAAGCACGGCTCCCACAAACTTATCATCGCCACAGGATTCATTGCAAAG
841  ---------+---------+---------+---------+---------+---------+
     CGTACCAAGGCCTTCGTGCCGAGGGTGTTTGAATAGTAGCGGTGTCCTAAGTAACGTTTC
      A  W  F  R  K  H  G  S  H  K  L  I  I  A  T  G  F  I  A  K
     AATGTGGAGGGGAAGATCACGACCCTGAAGCGCAACGGCAGCGACCTCAGCGCTACTACC
901  ---------+---------+---------+---------+---------+---------+
     TTACACCTCCCCTTCTAGTGCTGGGACTTCGCGTTGCCGTCGCTGGAGTCGCGATGATGG
      N  V  E  G  K  I  T  T  L  K  R  N  G  S  D  L  S  A  T  T
     TTGGGCGCACTGTTTCGCTGCGGCCACATCAGCATCTGGACGGACGTGGATGGCGTGTAC
961  ---------+---------+---------+---------+---------+---------+
     AACCCGCGTGACAAAGCGACGCCGGTGTAGTCGTAGACCTGCCTGCACCTACCGCACATG
      L  G  A  L  F  R  C  G  H  I  S  I  W  T  D  V  D  G  V  Y
     AGTGCGGACCCACGCAAGGTCCCCGAGGCTGTGTGCCTGCCCTCCATGACCTACCACGAG
1021 ---------+---------+---------+---------+---------+---------+
     TCACGCCTGGGTGCGTTCCAGGGGCTCCGACACACGGACGGGAGGTACTGGATGGTGCTC
      S  A  D  P  R  K  V  P  E  A  V  C  L  P  S  M  T  Y  H  E
     GCCTGGGAGATGAGCTACTTTGGCGCCAACGTGCTGCACCCACGCACCACCTTGCCAGCC
1081 ---------+---------+---------+---------+---------+---------+
     CGGACCCTCTACTCGATGAAACCGCGGTTGCACGACGTGGGTGCGTGGTGGAACGGTCGG
      A  W  E  M  S  Y  F  G  A  N  V  L  H  P  R  T  T  L  P  A
```

FIG. 4ii

```
       ATGAAGTACAACATCCCCATCACGATCCGCAACTTTTTCCGCCTGGAAGCACCAGGCACC
1141   ---------+---------+---------+---------+---------+---------+
       TACTTCATGTTGTAGGGGTAGTGCTAGGCGTTGAAAAAGGCGGACCTTCGTGGTCCGTGG
        M  K  Y  N  I  P  I  T  I  R  N  F  F  R  L  E  A  P  G  T
       CGGGTGAGCGATGTGGTCTCTGACTCTCAGGCATACGGCGGCCACGACCCAACCGTGAAG
1201   ---------+---------+---------+---------+---------+---------+
       GCCCACTCGCTACACCAGAGACTGAGAGTCCGTATGCCGCCGGTGCTGGGTTGGCACTTC
        R  V  S  D  V  V  S  D  S  Q  A  Y  G  G  H  D  P  T  V  K
       GGCTTTGCCACCATCGACAATGTGTCCCTCATCAGCATTGAGGGCACTGGCATGGTGGGT
1261   ---------+---------+---------+---------+---------+---------+
       CCGAAACGGTGGTAGCTGTTACACAGGGAGTAGTCGTAACTCCCGTGACCGTACCACCCA
        G  F  A  T  I  D  N  V  S  L  I  S  I  E  G  T  G  M  V  G
       GTGCCTGGTATCGCCAGCACCATCTTCTTTACCGTGCGCGATGCCAACATCAACGTCATC
1321   ---------+---------+---------+---------+---------+---------+
       CACGGACCATAGCGGTCGTGGTAGAAGAAATGGCACGCGCTACGGTTGTAGTTGCAGTAG
        V  P  G  I  A  S  T  I  F  F  T  V  R  D  A  N  I  N  V  I
       ATGATCAGCCAGGCCTCCAGCGAGCAGTCCATCTGCTTTGCCGTCAAGCAAGCAGACGGT
1381   ---------+---------+---------+---------+---------+---------+
       TACTAGTCGGTCCGGAGGTCGCTCGTCAGGTAGACGAAACGGCAGTTCGTTCGTCTGCCA
        M  I  S  Q  A  S  S  E  Q  S  I  C  F  A  V  K  Q  A  D  G
       CCGGCAGCTGTGCGGGCGCTGAGCCGCCGCTTTGCGGAGTCCATCAATGCAGGGCGCGTC
1441   ---------+---------+---------+---------+---------+---------+
       GGCCGTCGACACGCCCGCGACTCGGCGGCGAAACGCCTCAGGTAGTTACGTCCCGCGCAG
        P  A  A  V  R  A  L  S  R  R  F  A  E  S  I  N  A  G  R  V
       AGCAAGGTGGAGGCCATCGAGGGCTGCTGCGTGCTGGCAGCCGTGGGCCAGGGCATGGTG
1501   ---------+---------+---------+---------+---------+---------+
       TCGTTCCACCTCCGGTAGCTCCCGACGACGCACGACCGTCGGCACCCGGTCCCGTACCAC
        S  K  V  E  A  I  E  G  C  C  V  L  A  A  V  G  Q  G  M  V
       AACACCAAGGGCGTGAGCGCAACCATGATGGGTGCCCTGGCCAAGGCCAACGTAAACATC
1561   ---------+---------+---------+---------+---------+---------+
       TTGTGGTTCCCGCACTCGCGTTGGTACTACCCACGGGACCGGTTCCGGTTGCATTTGTAG
        N  T  K  G  V  S  A  T  M  M  G  A  L  A  K  A  N  V  N  I
       AAGGCCATCGCACAGGGCTCCTCTGAGTACAACATCACTGTGCTTGTGGACCAGAAAGAC
1621   ---------+---------+---------+---------+---------+---------+
       TTCCGGTAGCGTGTCCCGAGGAGACTCATGTTGTAGTGACACGAACACCTGGTCTTTCTG
        K  A  I  A  Q  G  S  S  E  Y  N  I  T  V  L  V  D  Q  K  D
```

FIG. 4iii

```
                AGCGAGCGTGCACTGCGTGCAGTGCACTCCCGCTTCTACTTGTCAGCCACTCCCCTGGGC
     1681       ---------+---------+---------+---------+---------+---------+
                TCGCTCGCACGTGACGCACGTCACGTGAGGGCGAAGATGAACAGTCGGTGAGGGGACCCG
                 S  E  R  A  L  R  A  V  H  S  R  F  Y  L  S  A  T  P  L  G
                ATTGGCCTCATTGGGCCAGGCCTGATTGGGGGGGCCTTGCTGGGGCAGATCAGGGACCAG
     1741       ---------+---------+---------+---------+---------+---------+
                TAACCGGAGTAACCCGGTCCGGACTAACCCCCCCGGAACGACCCCGTCTAGTCCCTGGTC
                 I  G  L  I  G  P  G  L  I  G  G  A  L  L  G  Q  I  R  D  Q
                GCTGAGACGCTGCGAAAGGACTTTGCCATCGACCTGCGAGTACTTGGCATTGCCTCTAGT
     1801       ---------+---------+---------+---------+---------+---------+
                CGACTCTGCGACGCTTTCCTGAAACGGTAGCTGGACGCTCATGAACCGTAACGGAGATCA
                 A  E  T  L  R  K  D  F  A  I  D  L  R  V  L  G  I  A  S  S
                AAAACAATGTTGCTCCAGGAGAAGGGAGTTGATTTGGAAAACTGGAGAGAGGAATTTCAA
     1861       ---------+---------+---------+---------+---------+---------+
                TTTTGTTACAACGAGGTCCTCTTCCCTCAACTAAACCTTTTGACCTCTCTCCTTAAAGTT
                 K  T  M  L  L  Q  E  K  G  V  D  L  E  N  W  R  E  E  F  Q
                CAGCGCGGGAGGCCTGTGGACTTGAAGGCCTTCAGCTCCGCCCTCGCCACCTCCTACATC
     1921       ---------+---------+---------+---------+---------+---------+
                GTCGCGCCCTCCGGACACCTGAACTTCCGGAAGTCGAGGCGGGAGCGGTGGAGGATGTAG
                 Q  R  G  R  P  V  D  L  K  A  F  S  S  A  L  A  T  S  Y  I
                CCCAACTGCGTGATCATCGACTGCACAGCCTCCGATGCACCCCCTGCGAGCTATTTGGAA
     1981       ---------+---------+---------+---------+---------+---------+
                GGGTTGACGCACTAGTAGCTGACGTGTCGGAGGCTACGTGGGGGACGCTCGATAAACCTT
                 P  N  C  V  I  I  D  C  T  A  S  D  A  P  P  A  S  Y  L  E
                TGGATGAAGCAAGGCATCCATGTAGTCACCCCCAATAAAAAGCTGGGCTCAGGACCACTT
     2041       ---------+---------+---------+---------+---------+---------+
                ACCTACTTCGTTCCGTAGGTACATCAGTGGGGGTTATTTTTCGACCCGAGTCCTGGTGAA
                 W  M  K  Q  G  I  H  V  V  T  P  N  K  K  L  G  S  G  P  L
                GCACAATATCAAGACATCAAGCAAGTTGGCCGAAACTCCTACACCCACTTCTTCTATGAG
     2101       ---------+---------+---------+---------+---------+---------+
                CGTGTTATAGTTCTGTAGTTCGTTCAACCGGCTTTGAGGATGTGGGTGAAGAAGATACTC
                 A  Q  Y  Q  D  I  K  Q  V  G  R  N  S  Y  T  H  F  F  Y  E
                GGCACTGTAGGCGCTGGCTTGCCCGTAATAGGCACCCTTAAACATCTTGTAGAGACTGGA
     2161       ---------+---------+---------+---------+---------+---------+
                CCGTGACATCCGCGACCGAACGGGCATTATCCGTGGGAATTTGTAGAACATCTCTGACCT
                 G  T  V  G  A  G  L  P  V  I  G  T  L  K  H  L  V  E  T  G
```

FIG. 4iv

```
             GATAAAGTAGAGAAAGTGGAAGGTATTTTCAGCGGTACCTTGTCATACATTTTCAACACC
      2221   ---------+---------+---------+---------+---------+---------+
             CTATTTCATCTCTTTCACCTTCCATAAAAGTCGCCATGGAACAGTATGTAAAAGTTGTGG
              D  K  V  E  K  V  E  G  I  F  S  G  T  L  S  Y  I  F  N  T

TTTGGAAGCGAGCGTCCCTTCAGCGAAGTTGTGGCGGATGCCAAGGTCAACGGCTACACT
      2281   ---------+---------+---------+---------+---------+---------+
             AAACCTTCGCTCGCAGGGAAGTCGCTTCAACACCGCCTACGGTTCCAGTTGCCGATGTGA
              F  G  S  E  R  P  F  S  E  V  V  A  D  A  K  V  N  G  Y  T

GAGCCCGACCCCCGTGATGACCTGAACGGCACTGATGTTGCCCGCAAGGTTACCATCCTA
      2341   ---------+---------+---------+---------+---------+---------+
             CTCGGGCTGGGGGCACTACTGGACTTGCCGTGACTACAACGGGCGTTCCAATGGTAGGAT
              E  P  D  P  R  D  D  L  N  G  T  D  V  A  R  K  V  T  I  L

ACGCGAGAGTGCGGCCTACAACTGGAGCTGTCTGACATTCCCATTGAGTCTTTGGTGCCT
      2401   ---------+---------+---------+---------+---------+---------+
             TGCGCTCTCACGCCGGATGTTGACCTCGACAGACTGTAAGGGTAACTCAGAAACCACGGA
              T  R  E  C  G  L  Q  L  E  L  S  D  I  P  I  E  S  L  V  P

GAGGCATTGCGAGGCTTGAACTCAAGTGAGGAATACATGGCACGGCTCCCAGAATTTGAT
      2461   ---------+---------+---------+---------+---------+---------+
             CTCCGTAACGCTCCGAACTTGAGTTCACTCCTTATGTACCGTGCCGAGGGTCTTAAACTA
              E  A  L  R  G  L  N  S  S  E  E  Y  M  A  R  L  P  E  F  D

GCAGAGATGGGGCGGCTTGCTGCAGAGGCAGAGGCAAGCGGGGAAGTCCTTCGATACGTG
      2521   ---------+---------+---------+---------+---------+---------+
             CGTCTCTACCCCGCCGAACGACGTCTCCGTCTCCGTTCGCCCCTTCAGGAAGCTATGCAC
              A  E  M  G  R  L  A  A  E  A  E  A  S  G  E  V  L  R  Y  V

GGCACTGTTGATGTGCAGAACAAAACTGGCAGCGTGGGATTAAAACAGTACCCCAGAAAC
      2581   ---------+---------+---------+---------+---------+---------+
             CCGTGACAACTACACGTCTTGTTTTGACCGTCGCACCCTAATTTTGTCATGGGGTCTTTG
              G  T  V  D  V  Q  N  K  T  G  S  V  G  L  K  Q  Y  P  R  N

CATGCATTCGCACAGCTAGAAGGATCTGACAACATCATTTCCTTTCAGACCTCTCGTTAC
      2641   ---------+---------+---------+---------+---------+---------+
             GTACGTAAGCGTGTCGATCTTCCTAGACTGTTGTAGTAAAGGAAAGTCTGGAGAGCAATG
              H  A  F  A  Q  L  E  G  S  D  N  I  I  S  F  Q  T  S  R  Y

AAGAGGCAACCGCTCTTCATCCGAGGGCCTGGTGCCGGAGCTGATGTGACGGCTGGTGGC
      2701   ---------+---------+---------+---------+---------+---------+
             TTCTCCGTTGGCGAGAAGTAGGCTCCCGGACCACGGCCTCGACTACACTGCCGACCACCG
              K  R  Q  P  L  F  I  R  G  P  G  A  G  A  D  V  T  A  G  G

GTGTTCTCTGACCTCTTGAAGCTGGCTGCTTACCTGGGTGCACCCTCTTGA
      2761   ---------+---------+---------+---------+---------+-
             CACAAGAGACTGGAGAACTTCGACCGACGAATGGACCCACGTGGGAGAACT
              V  F  S  D  L  L  K  L  A  A  Y  L  G  A  P  S  *
```

FIG. 4v

```
     ATGGCTGGGCTCAACTTTCCCATCGAAACTGCAGTGCAAGAGATGCCCAGTGATGGCAGG
  1  ---------+---------+---------+---------+---------+---------+
     TACCGACCCGAGTTGAAAGGGTAGCTTTGACGTCACGTTCTCTACGGGTCACTACCGTCC
      M  A  G  L  N  F  P  I  E  T  A  V  Q  E  M  P  S  D  G  R
     GACACGCTTTCATCTGCCCTGGAGCACATGCAAGTCAGGGACAGCCTAAAAATGTACAAC
 61  ---------+---------+---------+---------+---------+---------+
     CTGTGCGAAAGTAGACGGGACCTCGTGTACGTTCAGTCCCTGTCGGATTTTTACATGTTG
      D  T  L  S  S  A  L  E  H  M  Q  V  R  D  S  L  K  M  Y  N
     AACTTGGTGGAGCGTTGCTTCCGGGAGTGCAGCGAGGACATGCGCAGCAAAGCGCTGAGT
121  ---------+---------+---------+---------+---------+---------+
     TTGAACCACCTCGCAACGAAGGCCCTCACGTCGCTCCTGTACGCGTCGTTTCGCGACTCA
      N  L  V  E  R  C  F  R  E  C  S  E  D  M  R  S  K  A  L  S
     TCCAAGGAGGAGCAGTGTGTGGTCAAGTGCTGCGAGAAGTTTATGAATGTGACAGGGCGT
181  ---------+---------+---------+---------+---------+---------+
     AGGTTCCTCCTCGTCACACACCAGTTCACGACGCTCTTCAAATACTTACACTGTCCCGCA
      S  K  E  E  Q  C  V  V  K  C  C  E  K  F  M  N  V  T  G  R
     GTGGGCATGCGTTTCTCTGAATTCTTTTCACAAATGGAGGCAGCAGCCCAGCAGCATATG
241  ---------+---------+---------+---------+---------+---------+
     CACCCGTACGCAAAGAGACTTAAGAAAAGTGTTTACCTCCGTCGTCGGGTCGTCGTATAC
      V  G  M  R  F  S  E  F  F  S  Q  M  E  A  A  A  Q  Q  H  M
     GCGGAGATGCTCAAGCAGCAGGAGCAGCAGAGCAAATCATAG
301  ---------+---------+---------+---------+--  342
     CGCCTCTACGAGTTCGTCGTCCTCGTCGTCTCGTTTAGTATC
      A  E  M  L  K  Q  Q  E  Q  Q  S  K  *
```

SALT RESPONSIVE GENES USEFUL FOR GENERATING SALT RESISTANT TRANSGENIC PLANTS

RELATED APPLICATION DATA

This application is the U.S. national stage of PCT/IL2005/000933 filed on Sep. 1, 2005, which is based on and claims the benefit of U.S. Provisional Patent Application No. 60/606,414 filed on Sep. 2, 2004, which is incorporated herein in its entirety by this reference.

FIELD OF THE INVENTION

The present invention relates to transgenic plants capable of growing in conditions of high salinity. More specifically, the present invention relates to transgenic plants having high salt tolerance conferred by the expression of a *Dunaliella* salt-inducible or salt-responsive genes selected from the group consisting of eukaryotic initiation factor 3 (eIF3) sub-unit, also known as TRIP-1, NADPH dependent quinone reductase (QOR), aldo-keto reductase (AKR), bifunctional aspartate kinase-homoserine reductase (AK-HSD) and mitochondrial import membrane translocase subunit (TIM9), or a fragment, homolog or variant thereof.

BACKGROUND OF THE INVENTION

The progressive salinization of agricultural soils poses a major limitation for the growth and productivity of crop plants. Although engineering technologies involving drainage and supply of high quality water have been developed to overcome this problem, the existing methods are extremely costly and time-consuming. In many instances, due to the increased need for extensive agriculture, neither improved irrigation efficiency nor the installation of drainage systems is applicable. Moreover, in the arid and semi-arid regions of the world water evaporation exceeds precipitation. These soils are inherently high in salt and require vast amounts of irrigation to become productive. Since irrigation water contains dissolved salts and minerals, application of water further compounds the salinity problem.

Current attempts to enhance the salinity tolerance of model and crop plants are based on conventional breeding and selection of resistant variants. However, such breeding techniques typically require years to develop, are labor intensive and expensive. Moreover, thus far, these breeding and selecting strategies did not result in the mass production of tolerant varieties, suggesting that conventional breeding practices are not sufficient.

An alternative and attractive approach involves the genetic engineering of transgenic crops having enhanced salt tolerance. In recent years, advances in molecular biology have allowed mankind to manipulate the genetic complement of animals and plants. Genetic engineering of plants entails the isolation and manipulation of genetic material (typically in the form of DNA or RNA) and the subsequent introduction of the genetic material into plants. Such technology has led to the development of plants with increased pest resistance, plants that are capable of expressing pharmaceuticals and other chemicals and plants that express beneficial agricultural traits.

The primary negative effects imposed on plants by saline soil are the generation of osmotic imbalance due to ion uptake by the plant cell, and the toxicity of the ions. Sodium ions are toxic to plants due to their adverse effect on potassium nutrition, cytosolic enzyme activities, photosynthesis and metabolism. Different mechanisms function cooperatively to prevent accumulation of sodium ions ($Na^+$) in the cytoplasm of plant cells, namely restriction of $Na^+$ influx, active $Na^+$ efflux and compartmentalization of $Na^+$ in the vacuole. A comparison of ion distribution in cells and tissues of various plant species indicates that a primary characteristic of salt-tolerant plants is their ability to exclude sodium out of the cell or to take up sodium and sequester it in the cell vacuoles (Niu, X., et al., 1995 *Plant Physiol.* 109, 735-742). Although there is a wide spectrum of plant responses to salinity that are defined by a range of adaptations at the cellular and the whole plant levels, the mechanism of sodium transport appears to be fundamentally similar. At the cellular level, sodium ions are extruded by plasma membrane $Na^+/H^+$ antiporters that are energized by the proton gradient generated by the plasma membrane $H^+$-ATPases (PM $H^+$-ATPases). Cytoplasmic $Na^+$ may also be compartmentalized by vacuolar $Na^+/H^+$ antiporters. These transporters are energized by the proton gradient generated by the vacuolar $H^+$-ATPase and $H^+$-PPiase.

A mechanism that may underlie the adaptation or tolerance of plants to osmotic stresses is the accumulation of compatible, low molecular weight osmolytes such as sugar alcohols, special amino acids, and glycinebetaine. Recently, a transgenic study has demonstrated that accumulation of the sugar alcohol mannitol in transgenic tobacco conferred protection against salt stress (Tarczynski M C, et al., (1993). *Science* 259: 508-510). Two recent studies using a transgenic approach have demonstrated that metabolic engineering of the glycinebetaine biosynthesis pathway is not only possible but also may eventually lead to production of stress-tolerant plants (Holmstrom K O, et al., (1994) *Plant J* 6: 749-758).

In addition to accumulation of low molecular weight compounds, a large set of genes is subjected to transcriptional regulation, which leads to the accumulation of new proteins in vegetative tissue of plants under osmotic stress conditions. The expression levels of a number of genes have been reported to be correlated with desiccation, salt, or cold tolerance of different plant varieties of the same species. It is generally assumed that stress-induced proteins might play a role in tolerance, but the functions of many stress-responsive genes are unknown. Detecting stress-responsive genes as well as elucidating their function will not only advance our understanding of plant adaptation and tolerance to environmental stresses, but also may provide important information for designing new strategies and tools for crop improvement (Chandler P M and Robertson M., (1994) *Annu Rev Plant Physiol Plant Mol Biol* 45: 113-141).

The response of plants to salt stress has previously been studied in model plant species with sequenced genomes, including *Arabidopsis thaliana* (Consortium S. (2000) Nature 408: 796-815) and rice (Goff S A, et al. (2002) Science 296: 92-100; Yu J, et al. (2002) Science 296: 79-92). Differential genomic screens carried out in *Arabidopsis* and rice have shown that plants respond to salt stress by up-regulation of a large number of genes involved in diverse physiological functions.

For example, a homologue of sodium antiporter (AtNhx1) from the salt-sensitive plant *Arabidopsis thaliana* has been identified and characterized. Over expression of AtNhx1 in *Arabidopsis* as well as in fusion yeast shows increased salt tolerance due to better performance of salt compartmentation into the vacuole (Apse M P, et al. (1999) *Science* 285: 1256-1258). Zhang et al have shown that over expression of vacuolar $Na^+/H^+$ antiporter in *A. thaliana* and tomato plants led to a significant enhancement in salinity tolerance (Zhang H X & Blumwald E (2001) *Nature Biotechnology* 19: 765-768). Shi et al demonstrated that over expression of $Na^+/H^+$ antiporter SOS1 in plant plasma membranes improves salinity tolerance in *A. thaliana*, suggesting that a plasma membrane-type $Na^+/H^+$ antiporter is essential for plant salt tolerance. (Shi H, Lee B H & Zhu J K (2003) *Nat Biotechnology* 21: 81-85).

US Patent Application No. 20040040054 discloses polynucleotides encoding plant $Na^+/H^+$ antiporter polypeptides isolated from *Physcomitrella patens* and methods of applying these plant polypeptides to the identification, prevention, and/or conferment of resistance to various plant diseases and/or disorders, particularly environmental stress tolerance in plants, specifically salt stress.

US Patent Application No. 2002178464 discloses transgenic plants transformed with exogenous nucleic acid which alters expression of vacuolar pyrophosphatases in the plant, wherein the transgenic plants are tolerant to a salt. Specifically, the exogenous nucleotide encodes a vacuolar pyrophosphatase $H^+$ pump, AVP1.

International Patent Application No. WO 03/031631 discloses nucleic acids and nucleic acid fragments encoding amino acid sequences for salt stress-inducible proteins, protein phosphatases mediating salt adaptation in plants, plasma membrane sodium/proton antiporters, salt-associated proteins, glutathione peroxidase homologs associated with response to saline stress in plants, and early salt-responding enzymes such as glucose 6-phosphate 1 dehydrogenase and fructose-biphosphate aldolase in plants and the use thereof for, inter alia, modification of plant tolerance to environmental stresses and osmotic stresses such as salt stress, modification of plant capacity to survive salt shocks, modification of compartmentalization of sodium in plants, for example into the plant cell vacuole, modification of sodium ion influx and/or efflux, modification of plant recovery after exposure to salt stress, and modification of plant metabolism under salt stress.

U.S. Pat. No. 5,981,842 discloses a method of producing a cereal plant cell or protoplast useful for regeneration of a water stress or salt stress tolerant cereal plant by transforming the cereal plant cell or protoplast with a nucleic acid encoding a late embryogenesis abundant (LEA) protein. An LEA protein gene, HVA1, from barley (*Hordeum vulgare* L.) was transformed into rice (*Oryza sativa* L.) plants. The resulting transgenic rice plants accumulate the HVA1 protein in both leaves and roots. Transgenic rice plants showed significantly increased tolerance to water stress (drought) and salt stress. These studies demonstrate that, using a combination of breeding strategies and genetic manipulation, it is possible to generate plant crops having enhanced salt tolerance. However, all of the aforementioned methods rely on the isolation, characterization and over expression of genes from salt sensitive plant sources, and accordingly the success of such approaches relies on the expression of the plant genetic material, and the stability of the encoded proteins, in a salt environment.

Exceptionally salt tolerant (halotolerant) organisms may provide useful for identification of basic mechanisms that enhance salinity tolerance. A special example of adaptation to variable saline conditions is the unicellular green algae *Dunaliella*, a dominant organism in many saline environments, which can adapt to practically the entire range of salinities. *Dunaliella* responds to salt stress by massive accumulation of glycerol (its internal osmotic element), enhanced elimination of $Na^+$ ions, and accumulation of distinct proteins (Pick U et al. In A Lauchli, U Luthge, Eds, Salinity: Environment-Plants Molecules, Ed Acad. Pub. Dordrecht. Kluwer, pp 97-112, 2002). Since the cells of this genus do not possess a rigid cell wall, they respond to changes in salt concentration by rapid alterations in cell volume and then return to their original volume as a result of adjustments in the amounts of intracellular ions and glycerol. It has been reported that the adaptation to extreme salinity involves short-term and long-term responses. The former include osmotic adjustment by accumulation of large amounts of intracellular glycerol and efficient elimination of $Na^+$ ions by plasma membrane transporters. The latter involves synthesis of two extrinsic plasma membrane proteins, a carbonic anhydrase and a transferrin-like protein. These proteins are associated with acquisition of $CO_2$ and Fe, respectively, whose availability is diminished by high salinity. In addition, Ajalov et al reported on the isolation of a 64 kDA and 28 kDA salt-induced polypeptides from *Dunaliella salina* (Ajalov et al. (1996), *Biochemical Society Transactions,* 24(4), 5345).

Due to its remarkable ability to adapt to highly saline conditions, *Dunaliella* serves as a valuable model for the identification of basic mechanisms of salinity tolerance, and as a source for useful salt responsive genes.

The success of current plant breeding strategies which are based on genetic manipulation of genes from plant sources has been constrained due to the limited capability of many plants, specifically crop plants to adapt to saline conditions. There remains a need in the art to develop genetic engineering approaches that are superior to current techniques, and that would yield transgenic plants having high salt tolerance that are capable of growing in conditions of high salinity.

SUMMARY OF THE INVENTION

The present invention provides salt induced or otherwise salt responsive genes of the algae *Dunaliella* and transgenic plants comprising same. The transgenic plants of the present invention are by far superior as compared with other salt-tolerant plants known in the art. Specifically, previous attempts to generate salt-resistant transgenic plants rely on the over-expression of genes from plant sources. However, since plants are not well adapted to survive under highly saline conditions, the success of such approaches has been limited. The present invention takes advantage of the special features of the *Dunaliella salina* proteins, which have adapted to function at very high salt concentrations, to confer salt-resistance in plants.

The present invention discloses the identification of several salt-inducible or salt-responsive genes from the highly salt-tolerant green alga *Dunaliella*. Using a Fluorescent Differential Display (FDD) technology, applicants have characterized and cloned several salt-inducible or salt-responsive genes from the extremely halophilic alga *Dunaliella salina*. Database searches using the Blast program established unambiguous identities for these genes, namely A) eukaryotic initiation factor 3 delta subunit (eIF3 subunit, also known as TRIP-1); B) NADPH dependent quinone reductase (QOR); C) aldo-keto reductase (AKR); D) bifunctional aspartate kinase-homoserine reductase (AK-HSD); and E) mitochondrial import membrane translocase subunit (TIM9). Identification of these salt responsive genes, having different functions within the plant cell, revealed the existence of salt-imposed limitations on growth, which are distinct from the known toxic and osmotic effects of salt.

The optimal growth conditions for most *Dunaliella* species range from 0.5 to 2M NaCl, well above the maximal salinity range for growth of most plant species, which show reduced growth rates and other salt stress symptoms at a salinity of about 0.1M, and typically do not survive at salt concentrations above 0.2M. Therefore, *Dunaliella* proteins are adapted to function at high salinity. This special feature of these proteins was utilized in order to confer salt-tolerance in plants. As demonstrated herein, transformation of tobacco plants with a nucleic acid encoding eIF3 subunit or AK-HSD gives rise to a transgenic plant having an increased tolerance to salt as compared to a corresponding non-transgenic plant. The salt tolerance correlates with the expression of the *Dunaliella* salt-related genes in the transgenic plants, showing that plant adaptation to salt stress requires normal cell function and metabolic activities.

Thus, according to one aspect, the present invention provides an isolated nucleic acid encoding a *Dunaliella* salt inducible or salt responsive gene or a fragment, homolog or variant thereof.

According to one embodiment, the present invention provides an isolated nucleic acid comprising a polynucleotide encoding a *Dunaliella* salt-inducible or salt-responsive protein selected from the group consisting of eukaryotic initiation factor 3 (eIF3) subunit, NADPH dependent quinone reductase (QOR), aldo-keto reductase (AKR), bifunctional aspartate kinase-homoserine reductase (AK-HSD), and mitochondrial import membrane translocase subunit (TIM9), or a fragment, homolog or variant thereof.

In another embodiment, the present invention is directed to an isolated nucleic acid encoding a *Dunaliella* salt-inducible or salt-responsive protein or a fragment, homolog or variant thereof, wherein the nucleic acid comprises a polynucleotide selected from the group consisting of SEQ ID NO:1, SEQ ID NO:2, SEQ ID NO:3, SEQ ID NO:4 and SEQ ID NO:5, or a functionally active fragment or variant thereof.

In a currently preferred embodiment, the nucleic acid is isolated from a *Dunaliella salina* species.

In one embodiment, the nucleic acid encodes eukaryotic initiation factor 3 (eIF3) subunit, and is set forth in SEQ ID NO:1.

In another embodiment, the nucleic acid encodes NADPH dependent quinone reductase (QOR), and is set forth in SEQ ID NO:2.

In another embodiment, the nucleic acid encodes aldo-keto reductase (AKR), and is set forth in SEQ ID NO:3.

In another embodiment, the nucleic acid encodes bifunctional aspartate kinase-homoserine reductase (AK-HSD,) and is set forth in SEQ ID NO:4.

In another embodiment, the nucleic acid encodes mitochondrial import membrane translocase subunit (TIM9), and is set forth in SEQ ID NO:5.

According to another aspect the present invention provides to a construct comprising a nucleic acid encoding a *Dunaliella* salt-inducible or salt-responsive protein selected from the group consisting of eukaryotic initiation factor 3 (eIF3) subunit, NADPH dependent quinone reductase (QOR), aldo-keto reductase (AKR), bifunctional aspartate kinase-homoserine reductase (AK-HSD), and mitochondrial import membrane translocase subunit (TIM9), or a fragment, homolog or variant thereof.

According to another embodiment, the present invention provides a construct comprising a nucleic acid encoding a *Dunaliella* salt-inducible or salt-responsive protein, wherein the nucleic acid comprises a polynucleotide selected from the group consisting of SEQ ID NO:1, SEQ ID NO:2, SEQ ID NO:3, SEQ ID NO:4 and SEQ ID NO:5, or a functionally active fragment or variant thereof.

The construct preferably further includes regulatory elements controlling the expression of the nucleic acid within the plant cell including a promoter and a transcriptional terminator sequence, wherein the promoter, nucleic acid or nucleic acid fragment and the terminator sequence being operatively linked.

In another aspect the present invention provides a vector comprising a nucleic acid encoding a *Dunaliella* salt-inducible or salt-responsive protein or a fragment, homolog or variant thereof.

According to one embodiment, the nucleic acid encodes a *Dunaliella* salt-inducible or salt-responsive protein selected from the group consisting of eukaryotic initiation factor 3 (eIF3) subunit, NADPH dependent quinone reductase (QOR), aldo-keto reductase (AKR), bifunctional aspartate kinase-homoserine reductase (AK-HSD), and mitochondrial import membrane translocase subunit (TIM9), or a fragment, homolog or variant thereof.

According to yet another aspect the present invention provides a vector comprising an isolated nucleic acid encoding a *Dunaliella* salt-inducible or salt-responsive protein or a fragment, homolog or variant thereof, wherein the nucleic acid comprises a polynucleotide selected from the group consisting of SEQ ID NO:1, SEQ ID NO:2, SEQ ID NO:3, SEQ ID NO:4 and SEQ ID NO:5, or a functionally active fragment or variant thereof. Preferably the vector is a plant transformation vector.

Yet according to another aspect, the present invention provides a transgenic plant transformed with a nucleic acid encoding a *Dunaliella* salt-inducible or salt-responsive protein or a fragment, homolog or variant the. The transgenic plant has an increased tolerance to salt as compared to a corresponding non-transgenic plant.

According to one embodiment, the transgenic plant is transformed with a nucleic acid encoding a *Dunaliella* salt-inducible or salt-responsive protein selected from the group consisting of eukaryotic initiation factor 3 (eIF3) subunit, NADPH dependent quinone reductase (QOR), aldo-keto reductase (AKR), bifunctional aspartate kinase-homoserine reductase (AK-HSD), and mitochondrial import membrane translocase subunit (TIM9), or a fragment, homolog or variant thereof.

The present invention also provides a plant cell transformed with the nucleic acid, construct and/or vector of the present invention.

Further, also encompassed by the present invention is a plant seed which includes the nucleic acid, construct and/or vector of the present invention. The plant seed is advantageously used for breeding a plant having an increased tolerance to salt as compared to a corresponding plant grown from a seed produced by a corresponding non-transgenic plant.

The present invention also provides a method of producing a transgenic plant having an increased tolerance to salt as compared to a corresponding non-transgenic plant. The method comprises (a) transforming a plant cell with the nucleic acid, construct and/or vector of the present invention; and (b) regenerating the transformed cell into a plant having an increased tolerance to salt as compared to a corresponding non-transgenic plant.

In another aspect the present invention provides a method of modifying plant capacity to survive salt shock, comprising the step of introducing into one or more cells of the plant the nucleic acid, vector and/or construct of the present invention, thereby modifying the plant capacity to survive salt shock.

In still another aspect the present invention provides a method of modifying plant recovery after exposure to salt stress, comprising the step of introducing into one or more cells of the plant the nucleic acid, vector and/or construct of the present invention, thereby modifying the plant recovery after exposure to salt stress.

Preferably, the transformed transgenic plant of the present invention expresses the polypeptide product of the nucleic acid of the invention, i.e. a polypeptide selected from the group consisting of eukaryotic initiation factor 3 (eIF3) subunit, NADPH dependent quinone reductase (QOR), aldo-keto reductase (AKR), bifunctional aspartate kinase-homoserine reductase (AK-HSD) and mitochondrial import membrane translocase subunit (TIM9), or a fragment, homolog or variant thereof. The expression may be monitored by conventional methods known to a person skilled in the art, for example by extracting proteins from the transgenic plants and testing with antibodies directed against the specific protein.

Any suitable plant can be used to produce the transgenic plants of the present invention. Non-limiting examples include tobacco, maize, wheat, rye, oat, triticale, rice, barley, soybean, peanut, corn, cotton, rapeseed, canola, manihot, pepper, sunflower, tagetes, solanaceous plants, potato, eggplant, tomato, *Vicia* species, pea, alfalfa, sorghum, cucumber, lettuce, turf grass, ornamental (e.g., larger flowers, larger leaves), coffee, cacao, tea, *Salix* species, oil palm coconut, perennial grass and a forage crop. A currently preferred plant is a tobacco plant.

The transgenic plants are highly salt-resistant, and are able to grow in a concentration of salt that inhibits growth of a corresponding non-transgenic plant, for example a concentration of salt in the range of from about 0.1M to about 0.55M. For example, the transgenic plants of the present invention are adapted to grow in salt water, an environment typically too saline for many plant species. For example, in one embodiment, the transgenic plants of the present invention are adapted to grow in seawater.

Other objects, features and advantages of the present invention will become clear from the following description and drawings.

BRIEF DESCRIPTION OF THE DRAWINGS

The invention will be understood from the following detailed description in conjunction with the drawings, of which:

FIG. 1 shows the sequence of eukaryotic initiation factor 3 (eIF3) subunit cDNA from *Dunaliella salina* (SEQ ID NO: 1).

FIG. 2 shows the sequence of NADPH dependent quinone reductase (QOR) cDNA from *Dunaliella salina* (SEQ ID NO:2).

FIG. 3 shows the sequence of aldo-keto reductase (AKR) cDNA from *Dunaliella salina* (SEQ ID NO:3).

FIG. 4 shows the sequence of bifunctional aspartate kinase-homoserine reductase (AK-HSD) cDNA from *Dunaliella salina* (SEQ ID NO:4).

FIG. 5 shows the sequence of mitochondrial import membrane translocase subunit (TIM9) cDNA from *Dunaliella salina* is depicted in FIG. 5 (SEQ ID NO:5).

DETAILED DESCRIPTION OF THE INVENTION

Figure 6:
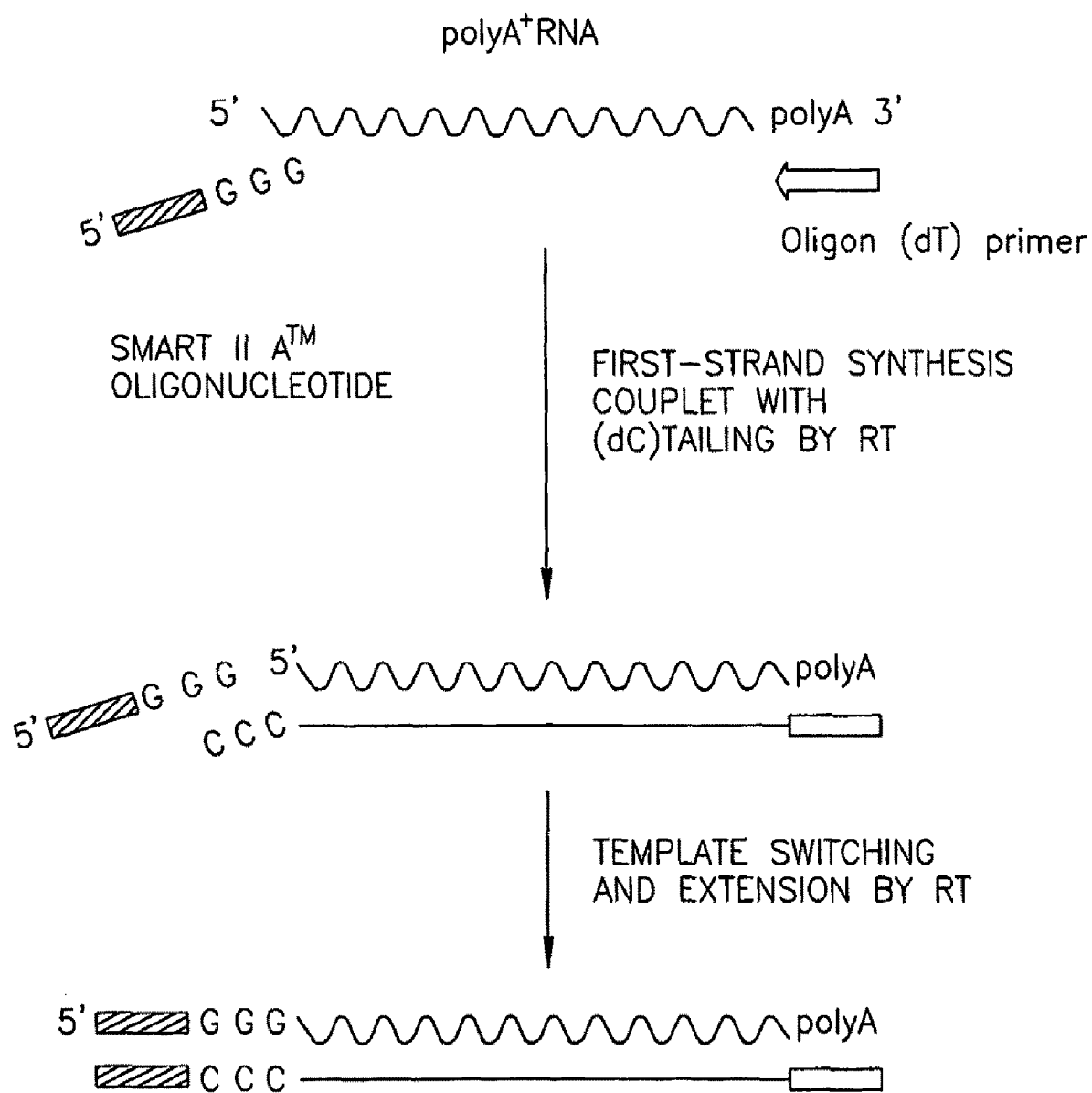
FIG. 6 shows a schematic illustration of the mechanism of SMART cDNA synthesis. Firs-strand synthesis is primed using a modified oligo (dT) primer. After reverse transcriptase reaches the end of the mRNA template, it adds several dC residues. The SMAPR II A oligonucleotide anneals to the tail of the cDNA and serves as an extended template for the PowerScript RT.

The present invention provides transgenic plants transformed with exogenous nucleic acid encoding a *Dunaliella* salt-inducible or salt-responsive protein selected from the group consisting of eukaryotic initiation factor 3 (eIF3) subunit, NADPH dependent quinone reductase (QOR), aldo-keto reductase (AKR), bifunctional aspartate kinase-homoserine reductase (AK-HSD) and mitochondrial import membrane translocase subunit (TIM9), or a fragment, homolog or variant thereof. The transgenic plants have increased tolerance to salt as compared to corresponding non-transgenic plants. The present invention further provides nucleic acids encoding the *Dunaliella* salt-inducible or salt-responsive proteins, constructs and vectors comprising same, and to a method of producing a transgenic plant having an increased tolerance to salt, a method of modifying a plant capacity to survive salt shock, and a method of modifying plant recovery after exposure to salt stress, by introducing the nucleic acids, constructs and/or vectors into one or more cells of the plant. Also provided by the present invention are plant cells comprising a nucleic acid, construct and/or vector according to the present invention, and plant seeds and progeny obtained from the transgenic plants.

The present invention makes a significant contribution to the art by providing new strategies to engineer salt-tolerance in crop plants. All previous attempts rely on the over-expression of genes from plant sources. In contrast, the present invention takes advantage of the special features of the *Dunaliella* proteins which have adapted to function at very high salt concentrations, to confer salt-resistance in plants. In addition, over expression of an endogenous plant gene frequently results in silencing of the transformed and/or native gene. Thus, the desired trait of salt resistance is not conferred to the plant by transformation of salt-resistant related genes from a plant source.

The present invention may be understood more readily by reference to the following detailed description of the preferred embodiments of the invention and the Examples included herein.

DEFINITIONS

The term "plant" is used herein in its broadest sense. It includes, but is not limited to, any species of woody, herbaceous, perennial or annual plant. It also refers to a plurality of plant cells that are largely differentiated into a structure that is present at any stage of a plant's development. Such structures include, but are not limited to, a root, stem, shoot, leaf, flower, petal, fruit, etc. As used herein, the term "salt" refers to any salt, such as NaCl, KCl, and/or $CaCl_2$. As used herein, "salt water" includes water characterized by the presence of salt, and preferably wherein the concentration of salt in the water is from about 0.2M to about 0.4M. In one embodiment, salt water refers to seawater.

As used herein, the term "salt-inducible" or "salt-responsive" refers to a protein or gene which is influenced by an altered environment of salt. For example, a salt-inducible or salt-responsive gene or protein may be over-expressed or its expression may be inhibited as a result of a rise or fall in salt concentration. Alternatively, the enzymatic activity of a salt-inducible or salt-responsive protein may be altered as a response to a rise or fall in salt concentration. For example, the protein may be induced or inhibited as a result of an alteration of salt concentration. Similarly, a salt-inducible or salt-responsive gene may by up regulated or down regulated as a response to a rise or fall in salt concentration.

The term "gene" refers to a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene. The fragments may range in size from a few nucleotides to the entire gene sequence minus one nucleotide. Thus, "a nucleic acid sequence comprising at least a part of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

The term "nucleic acid" as used herein refers to RNA or DNA that is linear or branched, single or double stranded, or a hybrid thereof. The term also encompasses RNA/DNA hybrids.

An "isolated" nucleic acid molecule is one that is substantially separated from other nucleic acid molecules which are present in the natural source of the nucleic acid (i.e., sequences encoding other polypeptides). Preferably, an "isolated" nucleic acid is free of some of the sequences which naturally flank the nucleic acid (i.e., sequences located at the 5' and 3' ends of the nucleic acid) in its naturally occurring replicon. For example, a cloned nucleic acid is considered isolated. A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

The term "construct" as used herein refers to an artificially assembled or isolated nucleic acid molecule which includes the gene of interest. In general a construct may include the gene or genes of interest, a marker gene which in some cases can also be the gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

The term "vector" as used herein encompasses both expression and transformation vectors. Vectors are often recombinant molecules containing nucleic acid molecules from several sources. In a preferred embodiment of this aspect of the invention, the vector may include a regulatory element such as a promoter and an enhancer that control or influence the transcription of the gene, a nucleic acid or nucleic acid fragment according to the present invention and a terminator that directs the termination of transcription; said regulatory element, nucleic acid or nucleic acid fragment and terminator being operatively linked.

By "operatively linked" is meant that said regulatory elements are capable of causing expression of said nucleic acid or nucleic acid fragment in a plant cell. Preferably, said regulatory element is upstream of said nucleic acid or nucleic acid fragment and said terminator is downstream of said nucleic acid or nucleic acid fragment.

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "transgenic" when used in reference to a plant or seed (i.e., a "transgenic plant" or a "transgenic seed") refers to a plant or seed that contains at least one heterologous gene in one or more of its cells. The term "transgenic plant material" refers broadly to a plant, a plant structure, a plant tissue, a plant seed or a plant cell that contains at least one heterologous gene in at least one of its cells.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

Transformation of a cell may be stable or transient. The term "transient transformation" or "transiently transformed" refers to the introduction of one or more exogenous polynucleotides into a cell in the absence of integration of the exogenous polynucleotide into the host cell's genome. Transient transformation may be detected by, for example, enzyme-linked immunosorbent assay (ELISA), which detects the presence of a polypeptide encoded by one or more of the exogenous polynucleotides. Alternatively, transient transformation may be detected by detecting the activity of the protein (e.g. β-glucuronidase) encoded by the exogenous polynucleotide. The term "transient transformant" refers to a cell which has transiently incorporated one or more exogenous polynucleotides. In contrast, the term "stable transformation" or "stably transformed" refers to the introduction and integration of one or more exogenous polynucleotides into the genome of a cell. Stable transformation of a cell may be detected by Southern blot hybridization of genomic DNA of the cell with nucleic acid sequences which are capable of binding to one or more of the exogenous polynucleotides. Alternatively, stable transformation of a cell may also be detected by enzyme activity of an integrated gene in growing tissue or by the polymerase chain reaction of genomic DNA of the cell to amplify exogenous polynucleotide sequences. The term "stable transformant" refers to a cell which has stably integrated one or more exogenous polynucleotides into the genomic or organellar DNA. It is to be understood that a plant or a plant cell transformed with the nucleic acids, constructs and/or vectors of the present invention can be transiently as well as stably transformed.

The terms "in vitro growth" or "grown in vitro" as used herein refer to regeneration and/or growth of plant material in tissue culture. Specifically, according to the present invention, a transformed plant cell or tissue is placed it in a sterile, (usually gel-based) nutrient medium, supplemented with the adequate additives to induce differentiation and plantlets growth. The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "homology", as used herein, refers to a degree of sequence similarity in terms of shared amino acid or nucleotide sequences. There may be partial homology or complete homology (i.e., identity). For amino acid sequence homology amino acid similarity matrices may be used as are known in different bioinformatics programs (e.g. BLAST, FASTA, Smith Waterman). Different results may be obtained when performing a particular search with a different matrix. Degrees of homology for nucleotide sequences are based upon identity matches with penalties made for gaps or insertions required to optimize the alignment, as is well known in the art (e.g. Altschul S. F. et al., 1990, J Mol Biol 215(3):403-10; Altschul S. F. et al., 1997, Nucleic Acids Res. 25:3389-3402).

The term "variant" as used herein refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The term "fragment" as used herein refers to a polypeptide having one or more deletions of amino acid residues relative to the sequence of the native polypeptide, so long as the activity of the native polypeptide is maintained. The amino acid residues may be deleted from the amino terminus and/or carboxy terminus and/or along the peptide sequence.

A special example of adaptation to hypersaline conditions is the unicellular green algae *Dunaliella*, a dominant organism in many saline environments, which can adapt to practically the entire range of salinities. As demonstrated herein, using a Fluorescent Differential Display (FDD) screen, Applicants have characterized and cloned several salt-inducible or salt-responsive genes from *Dunaliella salina*. These genes have been utilized to confer salt-resistance in plants.
Salt Responsive Genes of *Dunaliella* and Transgenic Plants Comprising Same Fluorescent Differential Display (FDD) of fluorescently labeled cDNA 3'-fragments was selected as the method of choice due to its high reliability and reproducibility. The method was applied essentially as described by the manufacturer (GenHunter Corporation, Catalogs of 1998/1999 and 2001/2002).

Over 1200 combinations of primers and total cDNAs from *Dunaliella* cells grown in a low- and high-salt medium were screened by PCR amplification/Genscan analysis. Candidate salt-inducible mRNAs, as represented by 3' fragments of corresponding cDNAs, were isolated from Fluoro-Imager scanned gels, checked for reproducibility and extent of salt-inducibility by quantitative RealTime PCR amplification. Confirmed clones served as a basis for cDNA sequence extension by several steps of 5' Rapid Amplification of cDNA Ends (5'-RACE), as detailed in the Experimental Details Section. Full-length cDNA clones were recovered by PCR with specific primers based on 5'- and 3'-terminal sequences of the compiled full-length sequences. The cDNAs were cloned into vectors offering versatile options for subsequent manipulations, towards the construction of effective plant vectors.

The FDD cDNA screen yielded about 20 salt-inducible genes, out of a total of several hundred cDNAs whose levels remained unchanged, or repressed in high salinity. Database searches using the Blast program established unambiguous identities for all but one of the cloned salt-induced *Dunaliella* genes. Identity assignments of the cDNAs reveal hitherto unknown aspects of salt tolerance and present novel tools and concepts for enhancing salt tolerance in plants.

Five cloned genes are classified herein according to their functions. The sequences of the encoded proteins are depicted in FIGS. 1-5, SEQ ID NOs. 6-10.
(i) Cellular Regulatory Functions: Growth Cell Cycle Control Stress Responses eIF3: Eukaryotic Initiation Factor 3 Delta Subunit (eIF3)

The subunit is also known as TRIP-1, or TGF-β receptor interacting protein 1. The sequence of eIF3 subunit cDNA from *Dunaliella salina* is depicted in FIG. 1, SEQ ID NO:1.

The gene cloned from *Dunaliella* encodes a ~320 amino acid long protein belonging to a large family of eukaryotic proteins, characterized by a variable number of a repeated WD (tryptophan-aspartate) amino acid motif. Proteins belonging to this family perform a large variety of crucial regulatory functions in animals, plants and yeasts, including growth and development, protein synthesis initiation, cell cycle control, signal transduction, and most importantly stress responses (Yu L et al., 2000, *Protein Science* 9: 2470-2476).

The *Dunaliella* gene product is homologous to a subunit of the multi-subunit eukaryotic initiation factor eIF3 that plays a pivotal role in the initiation step of protein synthesis in all eukaryotes. The protein is also involved in signal transduction from the TGF-β receptor in animals and the brassinosteroid receptor in plants (Jiang J & Clouse S D, (2001), *Plant J* 26: 35-45). A function most relevant to salt tolerance was uncovered in fission yeast where a homologous protein modulates an osmotic stress response of the S⇒M checkpoint of the cell cycle and relocalizes to cytoplasmic foci presumed to consist of a stress-protected protein biosynthetic machinery (Dunand-Sauthier I et al., *Mol Biol Cell*, (2002) 13: 1626-1640).

A protein belonging to the same family eIF3, and possibly identical to it, has been identified as highly salt-inducible in a proteomic analysis of algal cells growing constantly in low or high salt (Liska A J et al., *Plant Physiology*, (2004) 136: 2806-2817). The proteomics approach cannot distinguish between primary effects, namely gene products directly related to imparting an increased salt resistance, and secondary effects, namely any of a group of proteins up-regulated in response to various stresses including high salt.

The present invention now shows for the first time the ability of the *Dunaliella* eIF3 gene or gene product to confer salt resistance on another organism. It is now disclosed that plants transformed with this gene have increased resistance to salinity.

(ii) Antioxidant Defense Functions Against Salt-Induced Oxidative Stress

A. QOR: NADPH Dependent Quinone Reductase (Also Homologous to NADP+ Allylic Alcohol Dehydrogenase and Zeta-Crystallin Homolog).

The sequence of QOR cDNA from *Dunaliella salina* is depicted in FIG. 2, SEQ ID NO:2.

The gene cloned from *Dunaliella* is homologous to plant NADPH-dependent quinone reductases (QOR). Genes of this family are broadly conserved and thought to have evolved early to protect against oxidative damage associated with aerobic existence, particularly to abolish quinone-originating damage. The algal enzyme was found to be closely related not only to eukaryotic QOR proteins but also to a protein from an extremely halophilic archaea, *Halobacterium* sp. NCR-1. This resemblance suggests salt stability of the *Dunaliella* QOR.

The adverse effects of salt on plants and other photosynthetic organisms are ascribed to a large extent to salt-triggered oxidative-damage. Tolerance to salt stress has been associated with non-enzymic (mediated by reductants/scavengers such as ascorbate, glutathione, carotenoids, etc) and enzymic (active-oxygen-neutralizing) defense mechanisms that counteract the harmful effect of reactive oxygen species. The discovery of a salt-inducible QOR (as well as of AKR described below) links, for the first time, this class of proteins to salt tolerance and thus provides for a new tool for enhancing salt tolerance.

B. AKR: Aldo-Keto Reductase

The sequence of AKR cDNA from *Dunaliella salina* is depicted in FIG. 3, SEQ ID NO:3.

The *Dunaliella* gene encodes a ~310 amino acid protein belonging to the family of the aldo-keto reductases (Jez J M et al., (1997), *Biochem J* 326: 625-636). These broadly conserved enzymes catalyze primarily the NADPH-dependent reduction of carbonyl-containing substrates (aldehydes, aldoses, ketones) to their corresponding alcohols. AKRs were also implicated in detoxification of aldehyde toxins. The co-inducibility of the *Dunaliella* AKR, together with the functionally-related QOR (NADPH-dependent quinone reductase), that fulfills an antioxidant function in plants, leads to the conclusion that both enzymes could enhance salt tolerance by disarming molecular species generating oxidative damage.

(iii) Key Biosynthetic/Physiological Functions

AK-HSD: Bifunctional Aspartate Kinase-Homoserine Reductase

The sequence of AK-HSD cDNA from *Dunaliella salina* is depicted in FIG. 4, SEQ ID NO:4.

Aspartate is a common precursor for the biosynthesis of the essential amino acids methionine, threonine, isoleucine and lysine as well as for S-adenosyl methionine. The first two steps of this pathway are common to all branches. In plants, the first (aspartate kinase) and third (homoserine dehydrogenase) steps are catalyzed by a single bifunctional enzyme comprising a single polypeptide chain with two separate domains (Paris S et al., (2002), *Prot Exp Pur* 24, 105-110). As a key component of the branched biosynthetic pathway, AK-HSD is subject to differential feedback regulation by the various amino acid end products.

The cloned cDNA from *Dunaliella* is of ~2900 bp (the longest cDNA cloned) and encodes a ~900 amino acids protein. Its proposed functions in the context of salt tolerance are:

(i) Salinity levels as high as those tested in the induction experiments, i.e., 3.5 M NaCl, reduce photosynthetic efficiency. The induction of a key enzyme utilizing photosynthate leads to optimal re-distribution of photosynthate between different pathways to satisfy vital cellular processes such as protein synthesis.

(ii) The homoserine reductase activity converts aspartyl semialdehyde, the product of the second step of the pathway and a potential source of oxidative damage, to homoserine. A higher level of the bifunctional enzyme may help to lower the steady state level of the potentially harmful Asp semialdehyde.

(iv) Mitochondrial Transport and Chaperone Functions

TIM9: Mitochondrial Import Membrane Translocase Subunit: (Also Resembles Small Zn Finger-Like Protein)

The sequence of TIM9 cDNA from *Dunaliella salina* is depicted in FIG. 5, SEQ ID NO:5.

The cDNA cloned from *Dunaliella* encodes a protein homologous to Tim9, a component of the essential protein complex Tim9-Tim10 at the mitochondrial intermembrane space that mediates insertion of hydrophobic proteins at the inner membrane (Vial S et al., (2002), *J Biol Chem* 277: 36100-36108). The complex binds to the cargo proteins and performs chaperone functions. Very recently, plant proteins homologous of Tim9-Tim10 were shown to stimulate import of essential carrier proteins in mitochondria (Lister R et al., (2002), *Plant J* 30: 555-566).

High sodium in soil severely impairs mitochondrial function, especially in roots, that can be partly corrected by antioxidants and small heat shock proteins. The salt-inducibility of the *Dunaliella* tim9 provides strong evidence that the Tim9-Tim10 chaperone complex plays an important role in overcoming sodium toxicity to the essential import of proteins to mitochondrial compartments, and hence to cellular viability.

Evidence and considerations linking the cloned genes of the present invention to salt-tolerance are summarized in Table 1 below:

TABLE 1

| Protein | Function |
| --- | --- |
| eIF3 subunit | Osmotic/salt responses of cell cycle control and sub-cellular re-organization with presumed protective effect on protein synthesis. |
| QOR, AKR and possibly AK-HSR | Neutralizing oxidative stress generated by salt. |
| AK-HSR | Photosynthate distribution in essential biosynthetic pathways, possible antioxidant activity. |
| TIM9 | Maintenance of protein import in salt-challenged mitochondria |

The cloned cDNAs encode for conserved proteins/enzymes that fulfill critical functions in major cellular processes. Without wishing to be bound by any particular mechanism or theory, it is proposed that the induction of these genes in *Dunaliella* in response to salt implies that their over-expression serves as a means to overcome, or protect against direct or indirect salt-generated toxicity. Therefore, salt-inducibility could be one of the critical factors that distinguish the salt-tolerant *Dunaliella* from salt-sensitive plants, where none of the cloned genes homologs was found to be induced under salt and/or osmotic stresses.

Consequently, over-expression of these genes in plant hosts could mimic their protective effect in *Dunaliella*. Because the genes identified so far act in mostly different pathways, single, or double plant transformants typically exhibit an enhanced level of salt tolerance.

Although the invention is demonstrated with reference to the specific genes isolated from the species *Dunaliella salina* and the polypeptide products thereof, it is apparent to a person of skill in the art that other salt inducible or salt responsible genes isolated from *Dunaliella salina* are also encompasses within the scope of the present invention. It also apparent to a person skilled in the art that the *Dunaliella* species is not limited to this particular species, and that other species of salt-tolerant algae in general and from *Dunaliella* in particular may be utilized as a tool to confer salt-resistance to plants. Examples of such species include but are not limited to *Dunaliella acidophila*, *Dunaliella parva* and *Dunaliella bardawil*. Other algal species that can survive at high salinity and which can be utilized within the scope of the present invention include, for example *Halomonas*.

The nucleic acids can be isolated by any method known to a person of skill in the art, for example as described by Weiss et al (Weiss M & Pick U (1996) *Plant Physiol* 112: 1693-1702), incorporated by reference herein. The nucleic acid encompasses any nucleic acid fragment, homolog or variant of SEQ ID NOs. 1-5, and further encompasses any nucleic acid encoding the salt-inducible or salt-responsive protein selected from the group consisting of eukaryotic initiation factor 3 (eIF3) subunit, NADPH dependent quinone reductase (QOR), aldo-keto reductase (AKR), bifunctional aspartate kinase-homoserine reductase (AK-HSD), and mitochondrial import membrane translocase subunit (TIM9), or a fragment, homolog or variant thereof.

Genetic Constructs

According to another aspect the present invention provides a construct comprising a nucleic acid encoding a *Dunaliella* salt-inducible or salt-responsive protein selected from the group consisting of eukaryotic initiation factor 3 (eIF3) subunit, NADPH dependent quinone reductase (QOR), aldo-keto reductase (AKR), bifunctional aspartate kinase-homoserine reductase (AK-HSD), and mitochondrial import membrane translocase subunit (TIM9), or a fragment, homolog or variant thereof.

According to yet another aspect the present invention provides a construct comprising a nucleic acid encoding a *Dunaliella* salt-inducible or salt-responsive protein, wherein the nucleic acid comprises a polynucleotide selected from the group consisting of SEQ ID NO:1, SEQ ID NO:2, SEQ ID NO:3, SEQ ID NO:4 and SEQ ID NO:5, or a functionally active fragment or variant thereof.

According to a further aspect the present invention provides to a vector comprising a nucleic acid encoding a *Dunaliella* salt-inducible or salt-responsive protein selected from the group consisting of eukaryotic initiation factor 3 (eIF3) subunit, NADPH dependent quinone reductase (QOR), aldo-keto reductase (AKR), bifunctional aspartate kinase-homoserine reductase (AK-HSD), and mitochondrial import membrane translocase subunit (TIM9), or a fragment, homolog or variant thereof.

In another aspect the present invention provides a vector comprising an isolated nucleic acid encoding a *Dunaliella* salt-inducible or salt-responsive protein or a fragment, homolog or variant thereof, wherein the nucleic acid comprises a polynucleotide selected from the group consisting of SEQ ID NO:1, SEQ ID NO:2, SEQ ID NO:3, SEQ ID NO:4 and SEQ ID NO:5, or a functionally active fragment or variant thereof.

Preferably the vector is a plant transformation vector. In addition, the vector preferably further includes a promoter and a terminator, wherein the promoter, nucleic acid or nucleic acid fragment and terminator being operatively linked.

The vector may be of any suitable type and may be viral or non-viral. The vector may be an expression vector. Such vectors include chromosomal, non-chromosomal and synthetic nucleic acid sequences, e.g. derivatives of plant viruses; bacterial plasmids; derivatives of the Ti plasmid from *Agrobacterium tumefaciens*, derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable, integrative or viable in the plant cell.

The regulatory element and terminator may be of any suitable type and may be endogenous to the target plant cell or may be exogenous, provided that they are functional in the target plant cell.

Preferably the regulatory element is a promoter. A variety of promoters which may be employed in the vectors of the present invention are well known to those skilled in the art. Factors influencing the choice of promoter include tissue specificity of the vector, constitutive or inducible expression and the nature of the plant cell to be transformed (e.g. monocotyledon or dicotyledon).

Particularly suitable constitutive promoters include the Cauliflower Mosaic Virus 35S (CaMV 35S) promoter and derivatives thereof, the maize Ubiquitin promoter, and the rice Actin promoter. In a currently preferred embodiment, the present invention provides a construct wherein the gene of interest is operably linked to a 35 S promoter.

A variety of terminators which may be employed in the vectors of the present invention are also well known to those skilled in the art. The terminator may be from the same gene as the promoter sequence or from a different gene.

The genetic construct of the present invention can further comprise a reporter gene or a selection marker that is effective in the target plant cells to permit the detection of transgenic cells, tissues or plants containing the genetic construct. Such selection markers and reporter genes, which are well known in the art, typically confer resistance to one or more toxins or encode for a detectable enzymatic activity, respectively. The nptII gene, whose expression results in resistance to kanamycin or hygromycin antibiotics, which are generally toxic to plant cells at a moderate concentration, can be used as a selection marker. Alternatively, the presence of the desired construct in transgenic cells may be determined by means of other techniques that are well known in the art, including PCR, Southern and Western blots.

Those skilled in the art will appreciate that the various components of the vector are operatively linked, so as to result in expression of said nucleic acid or nucleic acid fragment. Techniques for operatively linking the components of the vector of the present invention are well known to those skilled in the art. Such techniques include the use of linkers, such as synthetic linkers, for example including one or more restriction enzyme sites.

In yet another aspect, the present invention provides transgenic plants comprising one or more plant cells which comprise a nucleic acid encoding a *Dunaliella* salt-inducible or salt responsive protein or fragment, homolog or variant thereof. The transgenic plants have an increased tolerance to salt as compared to corresponding non-transgenic plants.

In one embodiment, the transgenic plant is transformed with a nucleic acid comprising a polynucleotide encoding a *Dunaliella* eukaryotic initiation factor 3 (eIF3) subunit. In another embodiment, the transgenic plant is transformed with a nucleic acid comprising a polynucleotide encoding a *Dunaliella* NADPH dependent quinone reductase (QOR). In another embodiment, the transgenic plant is transformed with a nucleic acid comprising a polynucleotide encoding a *Dunaliella* aldo-keto reductase (AKR). In another embodiment, the transgenic plant is transformed with a nucleic acid comprising a polynucleotide encoding a *Dunaliella* bifunctional aspartate kinase-homoserine reductase (AK-HSD). In another embodiment, the transgenic plant is transformed with a nucleic acid comprising a polynucleotide encoding a *Dunaliella* mitochondrial import membrane translocase subunit (TIM9).

In one embodiment, the transgenic plant comprises one or more cells which include a nucleic acid set forth in SEQ ID NO:1. In another embodiment, the transgenic plant comprises one or more cells which include a nucleic acid set forth in SEQ ID NO:2. In another embodiment, the transgenic plant comprises one or more cells which include a nucleic acid set forth in SEQ ID NO:3. In another embodiment, the transgenic plant comprises one or more cells which include a nucleic acid set forth in SEQ ID NO:4. In another embodiment, the transgenic plant comprises one or more cells which include a nucleic acid set forth in SEQ ID NO:5.

The present invention also provides a plant cell transformed with the nucleic acid, construct and/or vector of the present invention. In one embodiment, the plant cell comprises a nucleic acid comprising a polynucleotide encoding a *Dunaliella* eukaryotic initiation factor 3 (eIF3) subunit. In another embodiment, the plant cell comprises a nucleic acid comprising a polynucleotide encoding a *Dunaliella* NADPH dependent quinone reductase (QOR). In another embodiment, the plant cell comprises a nucleic acid comprising a polynucleotide encoding a *Dunaliella* aldo-keto reductase (AKR). In another embodiment, the plant cell comprises a nucleic acid comprising a polynucleotide encoding a *Dunaliella* bifunctional aspartate kinase-homoserine reductase (AK-HSD). In another embodiment, the plant cell comprises a nucleic acid comprising a polynucleotide encoding a *Dunaliella* mitochondrial import membrane translocase subunit (TIM9).

Further, also encompassed by the present invention is a plant seed which includes the nucleic acid, vector and/or construct of the present invention. The plant seed is advantageously used for breeding a plant having an increased tolerance to salt as compared to a corresponding plant grown from a seed produced by a non-transgenic plant.

Also encompassed by the present invention are transgenic progeny of the transgenic plants described herein. Progeny transgenic plants are grown from seeds or shoots of the transgenic plants described herein.

The present invention further encompasses plants regenerated by tissue culture of the transgenic plants or transgenic cells of the present invention. The tissue culture comprises transgenic cells or protoplasts from a tissue selected from the group consisting of, but not limited to, leaves, pollen, embryos, roots, root tips, anthers, flowers, fruit and seeds.

The present invention also provides a method of producing a transgenic plant having an increased tolerance to salt as compared to a corresponding non-transgenic plant comprising (a) transforming a plant cell with the nucleic acid, construct and/or vector of the present invention; and (b) regenerating the transformed cell into a plant having an increased tolerance to salt as compared to a corresponding non-transgenic plant.

Techniques for incorporating the nucleic acids, constructs and/or vectors of the present invention into plant cells (for example by transduction, transfection or transformation) are well known to those skilled in the art. For example, *Agrobacterium* mediated plant transformation, particle bombardment, microparticle bombardment (e.g., U.S. Pat. No. 4,945,050; U.S. Pat. No. 5,100,792) protoplast transformation, gene transfer into pollen, injection into reproductive organs and injection into immature embryos can be used. Other techniques include electroporation to tissues, cells and protoplasts, protoplast fusion, and high velocity projectile introduction to cells, tissues, calli, immature and mature embryos. The choice of technique will depend largely on the type of plant to be transformed.

The exogenous nucleic acid can be introduced into any suitable cell(s) of the plant, such a root cell(s), stem cell(s) and/or leaf cell(s) of the plant.

According to another aspect the present invention provides a method of modifying plant capacity to survive salt shock, comprising the step of introducing into one or more cells of the plant the nucleic acid, vector and/or construct of the present invention, thereby modifying the plant capacity to survive salt shock.

In still another aspect the present invention provides a method of modifying plant recovery after exposure to salt stress, comprising the step of introducing into one or more cells of the plant the nucleic acid, vector and/or construct of the present invention, thereby modifying the plant recovery after exposure to salt stress.

Any suitable plant can be used to produce the transgenic plants of the present invention. Non-limiting examples include tobacco, maize, wheat, rye, oat, triticale, rice, barley, soybean, peanut, corn, cotton, rapeseed, canola, manihot, pepper, sunflower, tagetes, solanaceous plants, potato, eggplant, tomato, *Vicia* species, pea, alfalfa, sorghum, cucumber, lettuce, turf grass, ornamental (e.g., larger flowers, larger leaves), coffee, cacao, tea, *Salix* species, oil palm coconut, perennial grass and a forage crop. A currently preferred plant is a tobacco plant. In addition, the transgenic plants of the present invention can be grown in any medium which supports plant growth such as soil or water (hydroponically).

As demonstrated herein, the transformed transgenic plant of the present invention expresses the polypeptide product of the nucleic acids of the present invention. The expression may be monitored by conventional methods known to a person skilled in the art, for example by extracting proteins from the cells of the transgenic plants and testing the resulted protein mixture with antibodies directed against the specific protein.

In one embodiment, the transgenic plant expresses a *Dunaliella* eukaryotic initiation factor 3 (eIF3) or a fragment, homolog or variant thereof. In another embodiment, the transgenic plant expresses a *Dunaliella* NADPH dependent quinone reductase (QOR), or a fragment, homolog or variant thereof. In another embodiment, the transgenic plant expresses a *Dunaliella* aldo-keto reductase (AKR), or a fragment, homolog or variant thereof. In another embodiment, the transgenic plant expresses a *Dunaliella* bifunctional aspartate kinase-homoserine reductase (AK-HSD), or a fragment, homolog or variant thereof. In another embodiment, the transgenic plant expresses a *Dunaliella* mitochondrial import membrane translocase subunit (TIM9), or a fragment, homolog or variant thereof.

As mentioned above, the transgenic plants are highly salt-resistant, and are able to grow in a medium containing a salt concentration that inhibits growth of a corresponding non-transgenic plant, for example a concentration of salt in the range of from about 0.1M to about 0.55M, typically at a salt concentration ranging from about 0.2M to about 0.3M.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXPERIMENTAL DETAILS SECTION

Example 1

Salt-Inducible Genes/Proteins from *Dunaliella salina* as Tools to Enhance Plant Salt Tolerance Genomic Screens for Salt-Inducible Genes in *Dunaliella*

Fluorescent Differential Display (FDD) of fluorescently labeled cDNA 3'-fragments was selected as the method of choice due to its high reliability and reproducibility. FDD was employed essentially as described in catalogs 1998/1999 and 2001/2002 of the manufacturer, GenHunter Corporation.

Over 1200 combinations of primers and total cDNAs from cells grown in a low- or high-salt containing media were screened by PCR amplification/Genscan analysis. Candidate salt-inducible mRNAs, as represented by 3' fragments of corresponding cDNAs, were isolated from Fluoro-Imager scanned gels, checked for reproducibility and extent of salt-inducibility by quantitative RealTime PCR amplification. Confirmed clones served as a basis for cDNA sequence extension by several steps of 5'-RACE elongations-amplifications (see Example 2). Full-length cDNA clones were recovered by PCR with specific primers based on 5'- and 3'-terminal sequences of the compiled full-length sequences. The cDNAs were cloned into vectors offering versatile options for subsequent manipulations, towards the construction of effective plant vectors.

Cloned Salt-Inducible Genes/Proteins

The FDD cDNA screen yielded about 20 salt-inducible genes, out of a total of several hundred cDNAs whose levels remained unchanged, or repressed in high salinity. Database searches using the Blast program established unambiguous identities for all but one of the cloned salt-induced *Dunaliella* genes.

Identity assignments of the cDNAs reveal hitherto unknown aspects of salt tolerance and present novel tools and concepts for enhancing salt tolerance in plants.

Five cloned genes were classified according to their functions. The sequences of the five encoded proteins are shown in FIGS. 1-5.

(i) Cellular Regulatory Functions: Growth, Cell Cycle Control, Stress Responses

IF3: Eukaryotic Initiation Factor 3 Delta Subunit Homology eIF3-homologs were isolated as salt-inducible cDNAs in screens with two different primer pairs and initially considered to represent two independent clones. The cDNAs are practically identical in sequence and likely represent a single gene.

The sequence of eIF3 subunit cDNA (open reading frame) from *Dunaliella salina* (SEQ ID NO:1) and the encoded protein (SEQ ID NO:6) are depicted in FIG. 1.

(ii) Antioxidant Defense Functions Against Salt-Induced Oxidative Stress

A) QOR: NADPH Dependent Quinone Reductase;

The sequence of QOR cDNA (open reading frame) from *Dunaliella salina* (SEQ ID NO. 2) and the encoded protein (SEQ ID NO:7) are depicted in FIG. 2.

B) AKR: Aldo-Keto Reductase

The sequence of AKR cDNA (open reading frame) from *Dunaliella salina* (SEQ ID NO. 3) and the encoded protein (SEQ ID NO:8) are depicted in FIG. 3.

(iii) Key Biosynthetic/Physiological Functions

AK-HSD: Bifunctional as Aspartate Kinase-Homoserine Reductase

The sequence of AK-HSD cDNA (open reading frame) from *Dunaliella salina* (SEQ ID NO. 4) and the encoded protein (SEQ ID NO:9) are depicted in FIG. 4.

(iv) Mitochondrial Transport and Chaperone Functions

TIM9: Mitochondrial Import Membrane Translocase Subunit;

The sequence of TIM9 cDNA (open reading frame) from *Dunaliella salina* (SEQ ID NO. 5) and the encoded protein (SEQ ID NO:10) are depicted in FIG. 5.

Example 2

Preparation of cDNA by Rapid Amplification of cDNA Ends (RACE)

Previously conducted screens for salt-inducible genes yielded a group of partial-length cDNAs for potential salt-inducible genes from *Dunaliella*. Realtime RT-PCR analyses with these clones as templates and cDNAs for mRNAs from low or high-salt grown cells provided rigorous criteria for salt-inducibility. These segments were extended to the full length of the respective cDNAs by several extension steps using the 5' RACE (rapid amplification of cDNA ends) procedure. The sequences of the full length cDNAs were used to screen the NCBI database for homologous sequences, as described in Example 1.

Outline of the Procedure

The Smart Race cDNA Amplification method provides a novel tool for performing both 5'- and 3'-rapid amplification of cDNA ends (RACE). This method allows isolating the complete 5' sequence of the target transcript (cDNA) by eliminating the use of problematic adaptor ligation and enables the use of the first-strand cDNA directly in RACE PCR.

The method is based on a method for generating full-length cDNA in reverse transcription reactions. This is made possible by the joint action of the SMART II™ (BD Biosciences, Clontech, Calif.) oligonucleotide and PowerScript Reverse Transcriptase (RT).

PowerScript™ Reverse Transcriptase (RT) (BD Biosciences, Clontech, Calif.) is a variant of Moloney murine leukemia virus reverse transcriptase (MMLVRT) that, upon reaching the end of an RNA template, exhibits terminal transferase activity, adding 3-5 residues (predominantly dC) to the 3' end of the first-strand cDNA (FIG. 6).

The terminal stretch of dG residues (bold) of the SMART II oligonucleotide (5'-AAGCAGTGGTATCAACGCAGAGTACGCGGG, SEQ ID NO:11) can anneal to the dC-rich cDNA tail and serve as an extended template for RT. After PowerScript™ RT switches templates from mRNA molecule to the SMART™ oligonucleotide, a complete cDNA copy of the original RNA is synthesized with the additional SMART sequence at the end.

Figure 7I:
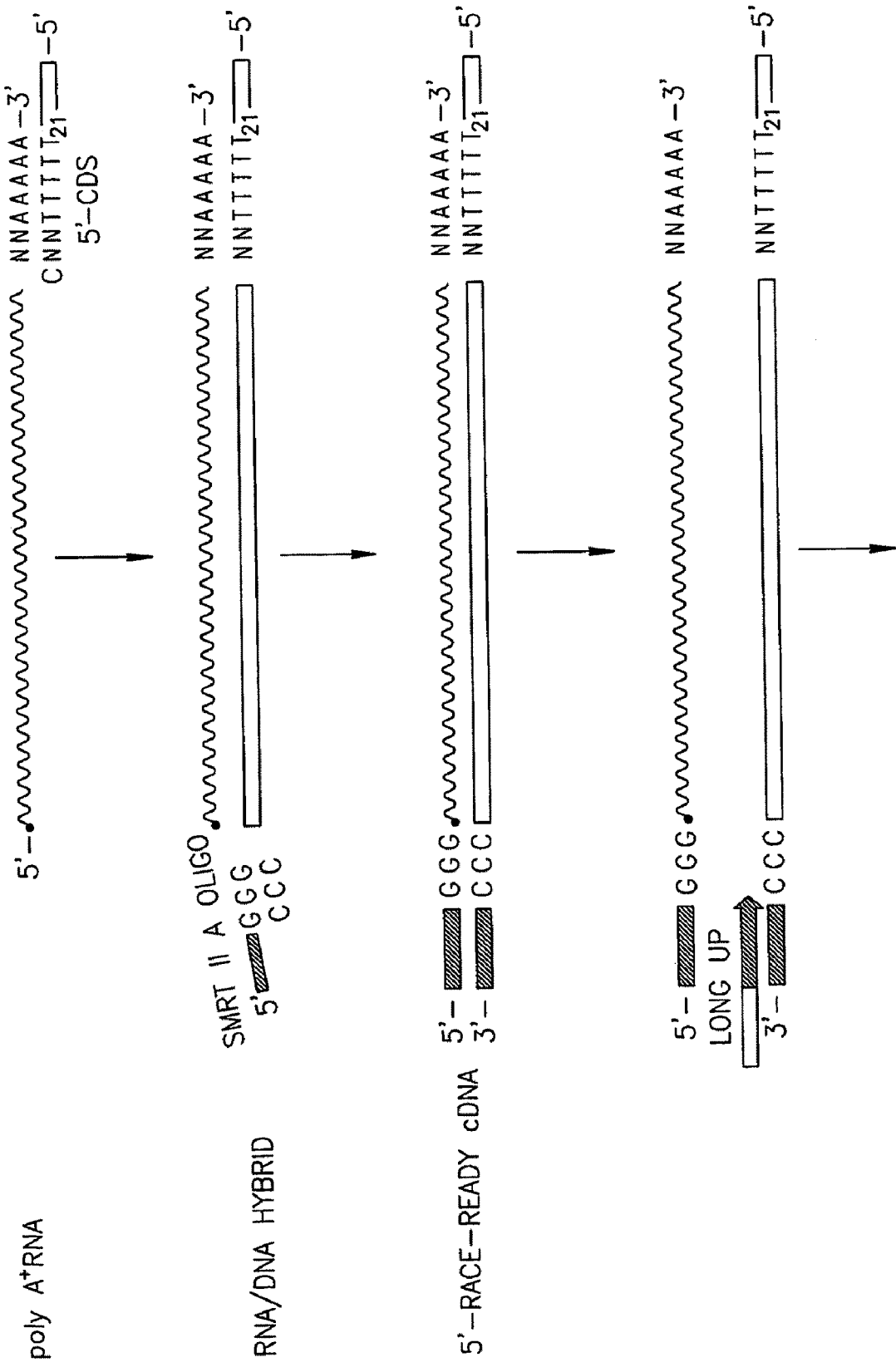
FIG. 7 shows a schematic illustration of 5-RACE PCR. Following reverse transcription, the first-strand cDNA is used directly in 5' RACE PCR reactions by using a universal primer, that includes the SMART II oligonucleotide sequence and Gene Specific Primers.
Figure 7I:
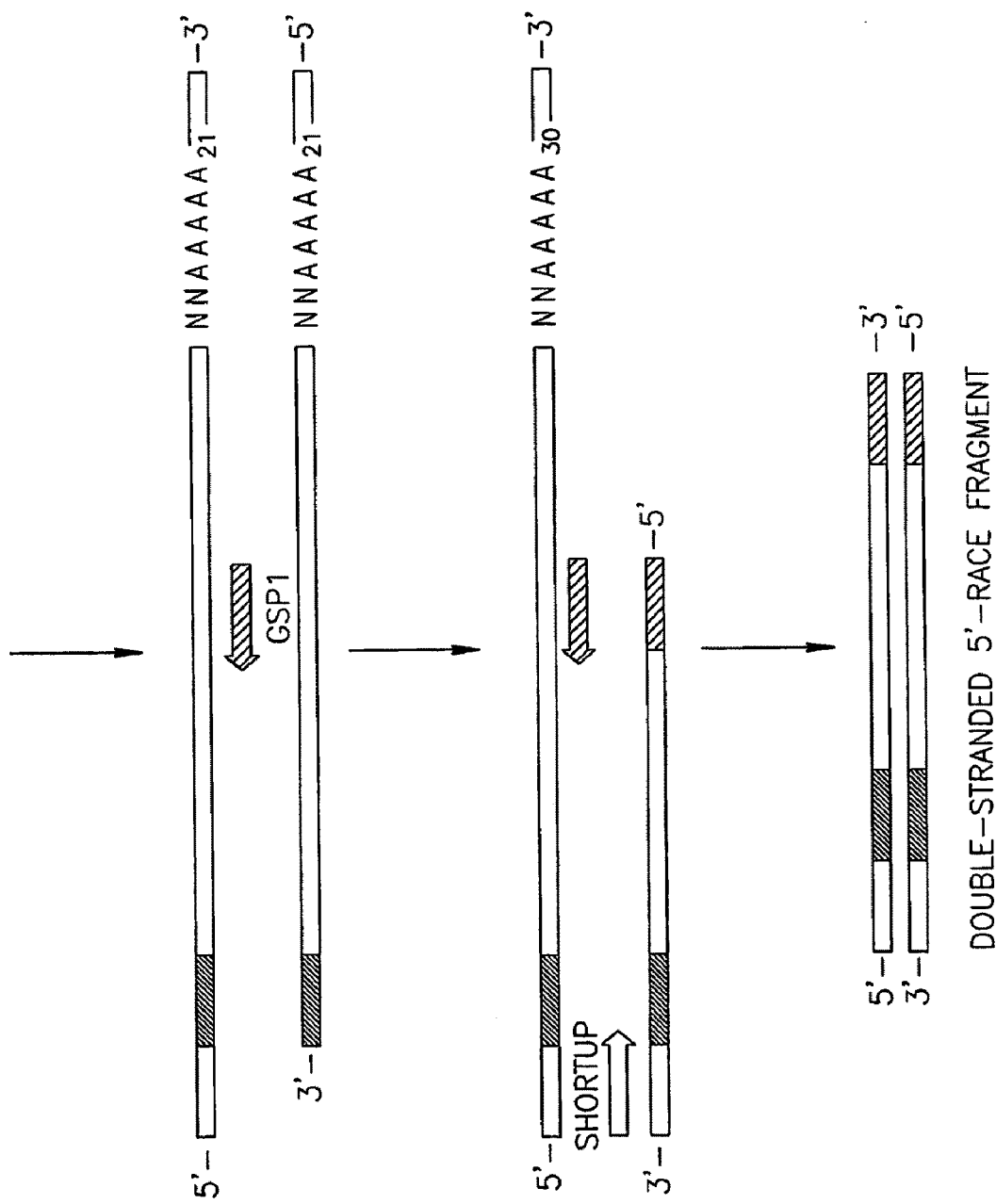

Following reverse transcription, the first-strand cDNA is used directly in 5' RACE PCR reactions by using a universal primer, that includes the SMART II™ oligonucleotide sequence, and Gene Specific Primers (GSPs) (FIG. 7).

```
Long Universal Primer (Long UP):
                                    (SEQ ID NO:12)
5'-CTAATACGACTCACTATAGGGCAAGCAGTGGTATCAACGCAGAG

T-3'
```

-continued

```
Short Universal Primer (Short UP):
                                            (SEQ ID NO:13)
5'-CTAATACGACTCACTATAGGGC-3'

(SEQ ID NO:14)
5'-RACE CDS (coding sequence) Primer (5'-CDS)

5'-(T)25N1N-3'
(N = A, C, G; or T; N1 = A, G, or C)
```

Primer Design:

Gene-Specific Primers (GSPs) should have a GC content of 50-70% and a Tm of at least 65° C. Whenever possible the Tm should be above 70° C. All primers should be 23-28 nucleotide long, and should not include self-complementary sequences which can fold back and form intramolecular base pairing. Similarly, primers that are complementary to the sequence of Universal Primer should be avoided.

Nested Primers:

The Universal and Gene Specific Primers generate in many cases nonspecific background. PCR using nested primers is necessary for specificity. In nested PCR, a primary amplification is performed with the outer primers and an aliquot of the primary PCR product is re-amplified using the nested (inner) primers.

Experimental and Results

Axenic cultures of *Dunaliella salina* were grown with shaking in a medium containing: 5 mM $KNO_3$, 5 mM $MgSO_4$, 50 mM $NaHCO_3$, 0.3 mM $CaCl_2$, 0.2 mM $KH_2PO4$, 1.5 µM $FeCl_3$, 6 µM EDTA, 0.8 µM $ZnCl_2$, 7 µM $MnCl_2$, 0.02 µM $CoCl_2$, 0.2 nM $CuCl_2$, and 0.5M or 3.5M NaCl, at 28° C. under continuous illumination of 20 $W/m^2$, by cool white fluorescent lamps. All manipulations were carried out under aseptic conditions.

Two Step NaCl-Induced Hyperosmotic Shock

A culture of *D. salina* was grown in one-liter medium containing 0.5 M salt (NaCl) (in a 4 l Erlenmeyer flask) up to a density of $10^6$ cells/ml. One half of this culture was centrifuged at 2000 g for 10 min at room temperature, and the pellets were frozen at −80° C. in aliquots of $5\times10^7$ cells. The other half of the culture was subjected to a two step hyperosmotic shock as follows: after 2 h growth in a medium containing 0.5 M NaCl the cells were transferred into a medium with 1.5 M NaCl and allowed to recover osmotically (criterion: microscope examination for mobility) for 2 h. Subsequently, the culture medium was adjusted to 3.5 M NaCl by adding medium stock solution containing 5 M NaCl. The cells were further incubated in 3.5 M NaCl medium for 8 h, centrifuged as above and stored at −80° C. in aliquots of $5\times10^7$ cells. This stock of cells was used for RNA isolation and SMART™ RACE cDNA amplification.

Total RNA Isolation

The success of the 5'-RACE technique depends on the integrity of the RNA.

Total RNA was prepared from cells harvested 8 h after the hyperosmotic shock by extraction with 1 ml TriReagent/$10^7$ cells (www.promega.com).

mRNA Isolation

Poly(A) mRNA was isolated from 200-300 mg total RNA by using the PolyATract® (Promega, Wis.) mRNA isolation procedure based on a biotinylated oligo(dT) primer. The hybrids are captured and washed at high stringency using streptavidin coupled to paramagnetic particles and a magnetic separation stand. The mRNA is eluted from the solid phase by the addition of ribonuclease-free deionized water (Promega, Wis.).

First-Strand cDNA Synthesis

The synthesis of first strand cDNA was performed according to the following manufacturer instructions:
1. Combine the following in a 0.5-ml microcentrifuge tube:
   1-3 µl RNA 1 µg/µl
   1 µl 5'-CDS primer
   1 µl SMART II™ A oligo
2. Add sterile water to a final volume of 5 µl.
3. Mix contents and spin the tubes briefly in a microcentrifuge.
4. Incubate the tube at 70° C. for 2 min.
5. Cool the tube on ice for 2 min.
6. Spin the tube briefly to collect the contents at the bottom.
7. Add the following to the reaction tube (already containing 5 µl).
   2 µl 5× First-Strand buffer
   1 µl DTT (20 mM)
   1 µl DNTP Mix (10 mM)
   1 µl PowerScript™ Reverse Transcriptase
   10µ ml Total volume
8. Mix the content of the tube by gentle pipetting.
9. Spin the tube briefly to collect the content at the bottom.
10. Incubate the tube at 42° C. for 1.5 hr.
11. Dilute the first-strand reaction product with Tricine-EDTA Buffer 1:50.
12. Heat the tube at 72° C. for 7 min.

Rapid Amplification of cDNA Ends (RACE) by Using Advantage-GC PCR Kit

Advantage-GC 2 Polymerase mix facilitates PCR amplification of GC-rich sequences that are difficult or impossible to amplify by conventional methods. *D. salina* represents one of such organisms that contain GC-rich regions that prevent their amplification by standard PCR techniques. Because these GC-rich sequences possess strong secondary structures that resist denaturation and prevent primer annealing, PCR often fails to yield any product. Advantage™-GC 2 PCR Kit (BD Biosciences—Clontech, Calif.) amplifies these problematic regions. The reaction was performed according to the following manufacturer instructions:

PCR Protocol
1. Combine the following reagents in a 0.5 ml PCR tube (50 µl final reaction volume)

| | |
|---|---|
| 5 × GC PCR Buffer | 10 µl |
| GC-Melt (5M) | 5 µl |
| DNA template | 1 µl (from total RNA; 5 µl from mRNA) |
| Primer 1 (10 pmol) | 1 µl |
| Primer 2 (10 pmol) | 1 µl |
| 50 × dNTP | 1 µl |
| 50 × advantage-GC Pol. Mix | 1 µl |
| $H_2O$ up to | 50 µl |

2. Mix well and spin the tube briefly to collect all the liquid in the bottom of the tube.
3. Commence thermal cycling using the following parameters:

| 5 cycles | |
|---|---|
| 94° C. | 1 min |
| 68° C. | 3 min |
| 5 cycles | |
| 94° C. | 1 min |
| 67° C. | 2 min |
| 72° C. | 3 min |

-continued

| 20 cycles | |
|---|---|
| 94° C. | 1 min |
| 66° C. | 2 min |
| 72° C. | 3 min |
| 72° C. | 7 min |

"Touchdown PCR" involves using an annealing temperature that is several degrees higher than the Tm of the primers during the initial PCR cycles. The annealing temperature is then reduced to the primer Tm for the remaining PCR cycles.

Characterization of RACE Products

Comparison of RACE products obtained with gene specific and nested gene specific primers prevents confusion and wasted effort in generation of the full-length cDNA. This verification is especially important in the case of multiple bands that may accompany the products of the extension amplification cycle obtained with the universal primer mix (UPM) and gene specific primers (GSP1) of the SMART II™ kit. In this case the products have to be compared with the products obtained using the nested universal primer (NUP) and nested primers NGSP1). This analysis determines which bands contain the correctly primed PCR products. The difference in mobility of the products corresponds to the positions of the outer and inner (nested) primers in the cDNA structure. In the case of multiple bands in the first amplification round (obtained with UPM and GSP1) some bands disappear upon amplification with NUP and NGSP1.

Example 3

Salinity Tolerance in Tobacco Plants Transformed with eIF3 Subunit

The eIF3 gene was cloned in a pGEM plasmid that was further cloned onto a plant transformation vector and introduced into *Agrobacterium* strain LBA4404. A mild strain of *Agrobacterium tumefaciense* (LBA 4404) harboring binary plasmid (pR-288 or pR-117 containing a selection marker cassette and a CaMV 35S promoter) was used for transformation. The cells were grown in 2YT medium containing 50 mg/l kanamycin and 50 mg/l rifampicin for 16-18 hours at 27±1° C. on rotary shaker (100 rpm). Acetosyringone was added to the final concentration of 100 µM 2 hours before transformation for pre-induction.

Figure 8:
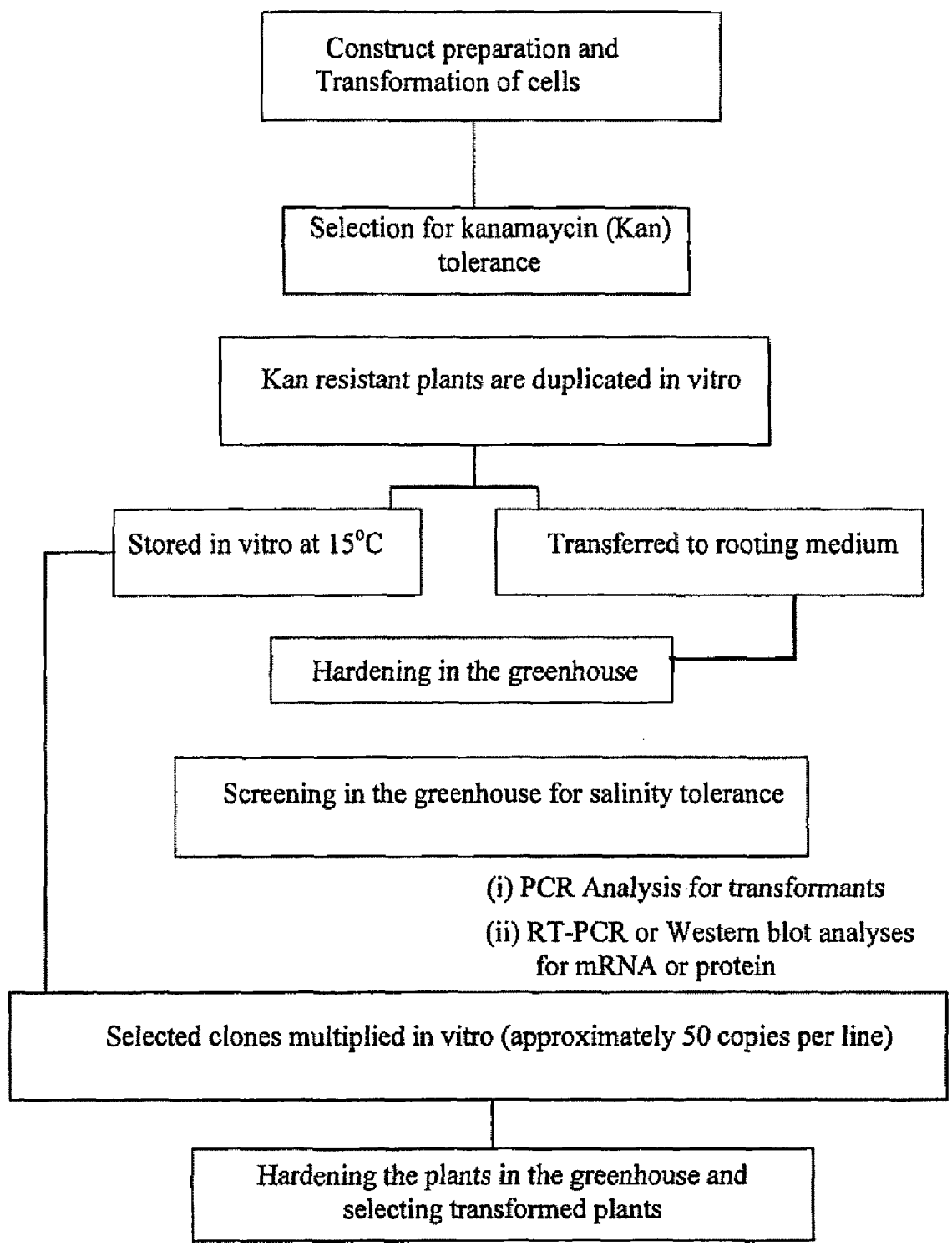
FIG. 8 schematically illustrates the analysis of transgenic tobacco plants expressing candidate genes from *Dunaliella* for tolerance to high levels of NaCl.

Tobacco plantlets were grown on MS medium supplemented with 3% sucrose and solidified with 6.5 g/l agar (Duchefa). The leaf segments were immersed in *Agrobacterium* culture and were wounded by cutting with a sharp blade. The leaf segments were co-incubated with *Agrobacterium* culture for 10 min. and subsequently blotted onto a filter paper (Whatman No. 42). Following co-incubation the leaf segments were placed in Petri dishes with regeneration medium containing MS minerals and vitamins, 1% manitol, 2% sucrose, 2 mg/l zeatin, 0.1 mg/l indoleacetic acid (IAA) and solidified with 6.5 g/l agar (Duchefa) for co-cultivation for 2 days. Following co-cultivation segments were transferred for recovery on the same medium supplemented with 300 mg/l cefotaxime for 7 days and then subcultured every 2 weeks on regeneration medium supplemented with 300 mg/l cefotaxime and kanamycin 50 mg/l, as selective agent. Plantlets having at least two leaves were transferred for rooting to MS medium supplemented with 3% sucrose, 300 mg/l cefotaxime and kanamycin 100 mg/l and solidified with 6.5 g/l agar (Duchefa), for 1 month. The plantlets were subsequently transferred to the same medium supplemented with kanamycin 200 mg/l for one more month and finally to the same medium supplemented with kanamycin 300 mg/l. Kanamycin-resistant plants were duplicated in vitro, stored at 15° C., transferred to rooting medium and taken for hardening in greenhouse as is illustrated schematically in FIG. 8.

Results

Figure 9:
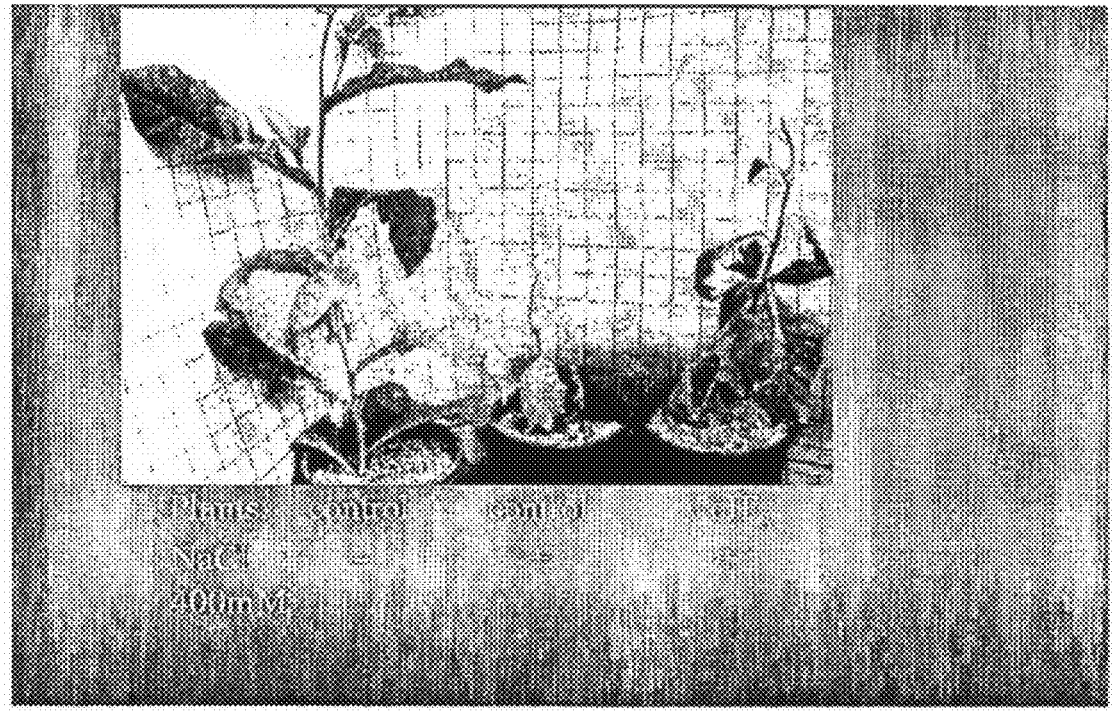
FIG. 9 is a picture of transgenic plants transformed with a *Dunaliella* eIF$_3$ subunit gene and control tobacco plants, grown with or without salt: control plant irrigated with a solution without salt (left); control plant irrigated with a solution containing 400 mM NaCl (middle), and eIF3 transformed plant irrigated with a solution containing 400 mM NaCl (right).

FIG. 9 shows a picture of salt-resistant and control tobacco plants cultivated with or without salt. Control plants were grown without additional salt (−) or with additional salt (+) (250 mM NaCl). Transgenic plants transformed with eIF$_3$ from *Dunaliella* were grown in the presence of 250 mM NaCl.

As clearly shown by the picture, control plants are unable to grow in the presence of salt, whereas plants transformed with the eIF$_3$ gene exhibit salt-resistant properties in the presence of this high salt concentration.

Example 4

Salinity Tolerance in Tobacco Plants Transformed with AK-HSD

Methods

The Bifunctional aspartate kinase-homoserine reductase (AK-HSD) in pGEM plasmids was cloned onto pR-288 or pR-117 binary plasmids containing a selection marker cassette and a 35 S promoter. The plasmid was transformed to *Agrobacterium* LBA4404 and transformed into SR1 tobacco lines as detailed in Example 3 above. All plants were selected by culturing the transformants in a medium containing increasing concentrations of kanamycin from 50-300 ppm as detailed above. Following transformation, the plants were grown in tissue culture and finally in a greenhouse for salinity resistance testing as indicated above. About 50 independent transgenic lines were examined.

Results

Figure 10:
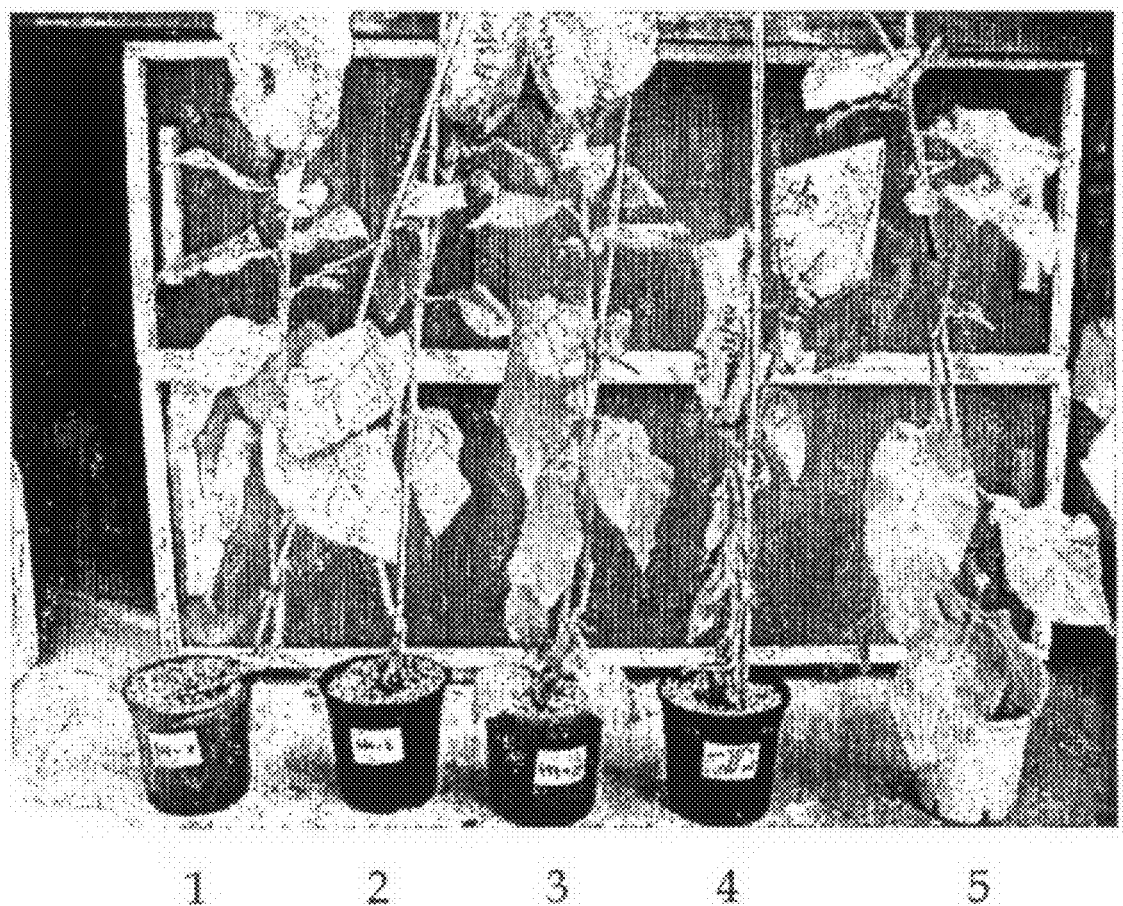
FIG. 10 is a picture of transgenic plants transformed with a *Dunaliella* AK-HSD gene and control tobacco plants, grown with or without salt. Plants 1-3—transgenic lines irrigated with solutions containing increased concentrations of salt. Plant 4—non-transgenic plant irrigated with a solution containing salt. Plant 5 is non-transgenic plant irrigated with non-salinated water.

FIG. 10 shows transgenic plants transformed with the AK-HSD construct and control plants grown under different salt conditions. Plants 1-3 are transgenic lines treated with increased concentration of salt (from 50-250 mM). Plant 4 is a non-transgenic plant irrigated with same salt concentrations and plant 5 is non-transgenic plant irrigated with non-salinated water. As shown by the picture, the AK-HSD construct confers salt tolerance in the transgenic plants.

It will be appreciated by a person skilled in the art that the present invention is not limited by what has been particularly shown and described hereinabove. Rather, the scope of the invention is defined by the claims which follow.

The invention claimed is:

1. An isolated nucleic acid molecule comprising a nucleotide sequence encoding a *Dunaliella* salt-inducible or salt-responsive protein eIF3 as set forth in SEQ ID NO: 6.

2. The nucleic acid molecule according to claim 1, wherein the salt-inducible or salt-responsive protein eIF3 is encoded by the nucleotide sequence as set forth in SEQ ID NO: 1.

3. A construct comprising the nucleic acid molecule of claim 1.

4. The construct of claim 3, further comprising a promoter and a terminator, wherein the promoter is operatively linked to the nucleotide sequence encoding said protein eIF3, and wherein said nucleotide sequence is operatively linked to the terminator.

5. A vector comprising the nucleic acid molecule of claim 1.

6. A vector comprising the construct of claim 3.

7. The vector of claim 6 further defined as a plant transformation vector.

8. A transgenic plant transformed with an isolated nucleic acid molecule comprising a nucleotide sequence encoding a *Dunaliella* salt-inducible or salt-responsive protein eIF3 as set forth in SEQ ID NO: 6.

9. The transgenic plant of claim 8, wherein the salt-inducible or salt-responsive protein eIF3 is encoded by the nucleotide sequence as set forth in SEQ ID NO: 1.

10. The transgenic plant according to claim 8, wherein said transgenic plant grows in a concentration of a salt that inhibits growth of a non-transgenic plant of the same species.

11. The transgenic plant according to claim 10, wherein the concentration of salt is from about 0.1M to about 0.55M.

12. The transgenic plant according to claim 10, wherein said transgenic plant is a tobacco plant.

13. A transgenic plant seed produced by the transgenic plant according to claim 8.

14. The transgenic plant seed according to claim 13, wherein the seed is used for breeding a transgenic plant having an increased tolerance to salt as compared to an untransformed plant of the same species.

15. A tissue culture comprising at least one plant cell or protoplast transformed with an exogenous nucleic acid molecule comprising a nucleotide sequence encoding a *Dunaliella* salt-inducible or salt-responsive protein eIF3 as set forth in SEQ ID NO: 6.

16. The tissue culture according to claim 15, wherein the least one plant cell or protoplast is obtained from a plant part selected from the group consisting of leaves, pollen, embryos, roots, root tips, anthers, flowers, fruit and seeds.

17. The tissue culture according to claim 15, wherein said tissue culture regenerates plants having an increased tolerance to salt as compared to an untransformed plant of the same species.

18. A plant regenerated from the tissue culture according to claim 15.

19. A plant cell transformed with an exogenous nucleic acid molecule comprising a nucleotide sequence encoding a *Dunaliella* salt-inducible or salt-responsive protein eIF3 as set forth in SEQ ID NO: 6.

20. The plant cell according to claim 19, wherein said plant cell grows in a concentration of a salt that inhibits growth of a non-transgenic plant cell of the same species.

21. The plant cell according to claim 20, wherein the concentration of salt is from about 0.1M to about 0.55M.

22. The plant cell according to claim 19, wherein said plant is a tobacco plant cell.

23. A method of producing a transgenic plant having an increased tolerance to salt as compared to a non-transgenic plant of the same species, comprising:
   (a) transforming at least one plant cell with a nucleic acid molecule comprising a nucleotide sequence encoding a *Dunaliella* salt-inducible or salt-responsive protein eIF3 as set forth in SEQ ID NO: 6, and wherein said protein is overexpressed in said plant cell; and
   (b) regenerating the transformed cell into a transformed plant having an increased tolerance to salt as compared to a non-transgenic plant of the same species.

24. The method according to claim 23, wherein the transgenic plant grows in a concentration of a salt that inhibits growth of a non-transgenic plant of the same species.

25. The method according to claim 24, wherein the concentration of salt is from about 0.1M to about 0.55M.

26. The method according to claim 23, wherein said transgenic plant is a tobacco plant.

27. The method according to claim 23, further comprising generating a transgenic seed from the transgenic plant, wherein said seed comprises said nucleic acid molecule.

28. The method according to claim 27, wherein the seed is used for breeding a plant having an increased tolerance to salt as compared to a non-transgenic plant of the same species.

* * * * *

SEQUENCE LISTING

<160> NUMBER OF SEQ ID NOS: 14

<210> SEQ ID NO 1
<211> LENGTH: 975

```
<212> TYPE: DNA
<213> ORGANISM: Dunaliella salina

<400> SEQUENCE: 1
atgaggcctt acctgctcaa gggccatgat agacccctta cccaagtaaa gttcaaccgc      60
gagggagacc ttttcgtgac ctgtgccaag aacaaccagt catgcctgtg gtggtcagat     120
gatggaaagc gtgtgggcac ctttgagggt cacaatggtg ctgtgtggag ctgcgacatg     180
acatgggagt ctgaccggct catcaccgcc tctgccgacc agacagtccg gatatgggac     240
atgaccaatg gcaaggagca gttccagttc aagatggggg agccatgccg cgcatgcaac     300
ctcagcttgg gggagcagat gcttgccttc accactgacg ctttcatggg cagctccccc     360
atggttcact ggctaagct ggaagacgac ctctcccaac aaactaccaa gactgtgctc      420
ggcatacaag ctcctaaggg ccgcattacg cgggtgttct ggtcagatat gaaccgcaca     480
ctagtgacct cgcatgatgg tggattcatg cgcaagtggg attcagagac cgggaagatg     540
ctgttagaga agcaagtgca tgagggcgac atccaagaca tgcagatgtc ccccgatggt     600
gcctacttca tcacagcctc cttagacaaa actgccaagc tcgtggacgc tgtggagctt     660
gaagccttga gacgtacaa gactgggcgc tttgtacaat ctgcagccat ttcaccgctg      720
tttgaccatg tattgctggg gggaggtcag gatgcttctc aagtgacaac gacctcctct     780
aaggctggcg ttttgaggc gcgcttcttt cacaagattt accaggaaga atttggaaac     840
gtaagagggc atttcggacc tatcaacact gtggcattcc atccgagtgg aaaaagcttc     900
ttgacaggtg gagaggatgg atatgtgcgc ttgcaccatt ttgacctcga ttacttcacc     960
acgaaattct tctga                                                      975

<210> SEQ ID NO 2
<211> LENGTH: 1071
<212> TYPE: DNA
<213> ORGANISM: Dunaliella salina

<400> SEQUENCE: 2
atggcttgca aggctcagac ggtgctgttc aaggagtacg tggaggtcgg cgaggtccca      60
cctgacaact tccagctaag gacaatcgat ctacccgccc tgaaggatgg cgaggtcctt     120
cttgagctgc agtacctgag tgtggatcct acatgcgtg gccgcatgcg caatgcagca      180
ggctactttg ttgggccctt tgtgccaggc gaggccctca gtggaggtgg agttgtagtt     240
gtcaaggaga gcaaggctcc cggcattgag aagggcaagt tctacagtgg catggtcccc     300
tggacttccc ctcaaatcgc aaccaaggca cagatggagc agatgcagcc tgtagacact     360
gacatcctca gttggctaa gctgccccctg tccggatacg ctggtgtgtt cggcctgacg     420
ggcatgacag cgtatgcctc actcaccagg attggcaagc caaagaaggg agagactgtg     480
tttgtctcgg gtgctgctgg ggctgttggc atgattgtgg ccagatgtg caagaatgtg      540
tacgatgca aggtggttgg ctctgcggga agtgaggaca aggtggagtt cctgacaaag      600
gagttgggct cgacgcggc ttggaactac aagacaatgc ccaccttgga tgctttgaac       660
aagttctgcc ctgaaggcat tgacatgtac tacgagaatt ttggcggtga gcagctagag     720
gccgcactcg aaaagtgcag ggaaaatgca cgcattgtgt gctgcggtat gatctcacaa     780
tacaacaaga agggagatga ccgctatggc gtgaagaact ggcgaacgt ggtgttcaag      840
aagatcaaga tggagggctt cttgctgttc aattcctgc ctgaggttgt tcctgaattc       900
tttgagcact ccccaagtg gatagctgag ggcaagatca aggacacaga gtacgttgtc     960
aaaggcggct tggcgaatgc tggccaggct ttctgcgaca tgatggccgg aaagaacaag    1020
```

```
ggcaaggctg tggtgaagtg cgtggacaag gaccctattg tggggaacta a          1071
```

<210> SEQ ID NO 3
<211> LENGTH: 1044
<212> TYPE: DNA
<213> ORGANISM: Dunaliella salina

<400> SEQUENCE: 3

```
atgtctaccg ccaatgtgca ggtgcagcag ggtgacaagc cccagcccgt gaagaccggc    60
aacaccaatg agcctgacta cgtgaggctg tccaacggcg tgctcatgcc cttgattggc   120
tacggcacct tccagctgca agatgcagac atggtcaagc aagctttgga ggtgggctac   180
cgccacttag actgtgcctc cctgtatggc aaccaggagc tcgtcggcag ggcattgcc    240
agctggattg ctgcagaccc cagcaagaac aagcgcgagg acctgtttgt gaccagcaag   300
attttaatg atgagcaccg gccagagctg ctgcgcaagt cagcggagaa gagcattgct   360
gagctaggga ccaagtacct ggacctgctg ctgctgcact ggcccaatgc cttcaagcct   420
ggatcaggca gctccttcca tggtgacgtg tgcccagcag agggcgagaa gcccctgga    480
tgcgtcgtgt ttgatgatga ggtcacccac gagcagacct ggcgcgccat ggagaagctg   540
gtggacgatg gtctggtgcg atgcattggc ctgtccaact tcagccacaa ggaggtgacc   600
cacatctgca atattgccag gatcaagcct accatcaacg agattgagct acaccccttc   660
ctggcacaga aggagtttgt ggcttggtgc gcgagcatgg gagtgacctg cctggcatac   720
ggtcccctcg gcggccccaa cgcttacctc cccaacgacc tgctgcccca ccccaccgtc   780
accaaggttg ctcaggaggc cggcaagacc aacggccgga tcctggtgaa gtggagcgtc   840
cagcgcggcg tgcctgtcct ggtgaagacc ggcactgcct ctcgcctgaa ggagaacctg   900
tggggcatga tggactacaa gctgaccgac gagcagatgg cggctctaga ctctttggaa   960
aacggcaagc ggcttgtgac tgtcccgtgg aagaagtggg agactgagcc cgttcctgac  1020
cctgtccctt ccacgaaggc ttga                                         1044
```

<210> SEQ ID NO 4
<211> LENGTH: 2811
<212> TYPE: DNA
<213> ORGANISM: Dunaliella salina

<400> SEQUENCE: 4

```
atgcttctgc gggccaattg tgctgcaggg ctgggatgca aagcgtcttc cggaaagacg    60
cctgcagctg ctcccgcaaa tgtcgctggt ttcaccgcgc agcactctgc ctgcttcgga   120
aaggcgtcca gctccacccg taatcatcat catgtcatca cccgctcct cccctcgtgc    180
ccagctcccc tcatgcccca agcagcccac agcagcgcca tctgccgagc agtagttgcc   240
cctgtggaga cggaggcagg gggtgccccc tttcagcgcg gttccggctg gcgctgcac    300
aagtttggcg gcacttgcat ggccgctgct gagcgcattg ccggggcaag caagctgatg   360
attgacatca accctgatgc agagggaaag gtggccgttg tgagcgcgat gggctcacac   420
ccgacttcgc ccctgaaggt gacagacgtg atcctccaga tgatcgccaa ggctgagcgc   480
caggaccagc gcttcctgct agacctggcc gcaccgcaag ataagcacgt tgactccgcc   540
aaggagctgt gggcgagag caaggagctg acctactttg tgggccgctt gctagaggac   600
atcaacaacc tgaaggcgat gctgaacgcc atgagcatcc cggtatgac cacagaggca   660
ttctcggact atgtggtggg ccacggcgag ctgtggagcg cgcagctcat ggcattgtac   720
tgccagcagc tgggcgcaga ctgtgtcttc atggacgcgc gcgatgtgct ggttgtgtcc   780
```

```
cccactagcg atggcaccag cgtggatttg gtggaggatg cgtccaacgc gcgcttggac    840
gcatggttcc ggaagcacgg ctcccacaaa cttatcatcg ccacaggatt cattgcaaag    900
aatgtggagg ggaagatcac gaccctgaag cgcaacggca gcgacctcag cgctactacc    960
ttgggcgcac tgtttcgctg cggccacatc agcatctgga cggacgtgga tggcgtgtac   1020
agtgcggacc cacgcaaggt ccccgaggct gtgtgcctgc cctccatgac ctaccacgag   1080
gcctgggaga tgagctactt tggcgccaac gtgctgcacc acgcaccac cttgccagcc    1140 atgaagtaca acatccccat cacgatccgc aacttttttcc gcctggaagc accaggcacc   1200
cgggtgagcg atgtggtctc tgactctcag gcatacggcg ccacgaccc aaccgtgaag    1260 ggctttgcca ccatcgacaa tgtgtccctc atcagcattg agggcactgg catggtgggt   1320
gtgcctggta tcgccagcac catcttcttt accgtgcgcg atgccaacat caacgtcatc   1380
atgatcagcc aggcctccag cgagcagtcc atctgctttg ccgtcaagca agcagacggt   1440
ccggcagctg tgcgggcgct gagccgccgc tttgcggagt ccatcaatgc agggcgcgtc   1500
agcaaggtgg aggccatcga gggctgctgc gtgctggcag ccgtgggcca gggcatggtg   1560
aacaccaagg gcgtgagcgc aaccatgatg ggtgccctgg ccaaggccaa cgtaaacatc   1620
aaggccatcg cacagggctc ctctgagtac aacatcactg tgcttgtgga ccagaaagac   1680
agcgagcgtg cactgcgtgc agtgcactcc cgcttctact tgtcagccac tccctgggc    1740 attggcctca ttgggccagg cctgattggg ggggccttgc tggggcagat cagggaccag   1800
gctgagacgt tgcgaaagga cttttgccatc gacctgcgag tacttggcat tgcctctagt   1860
aaaacaatgt tgctccagga gaagggagtt gatttggaaa actggagaga ggaatttcaa   1920
cagcgcggga ggcctgtgga cttgaaggcc ttcagctccg ccctcgccac ctcctacatc   1980
cccaactgcg tgatcatcga ctgcacagcc tccgatgcac cccctgcgag ctatttggaa   2040
tggatgaagc aaggcatcca tgtagtcacc cccaataaaa agctgggctc aggaccactt   2100
gcacaatatc aagacatcaa gcaagttggc cgaaactcct acacccactt cttctatgag   2160
ggcactgtag gcgctggctt gcccgtaata ggcacccctta acatcttgt agagactgga    2220 gataaagtag agaaagtgga aggtattttc agcggtacct tgtcatacat tttcaacacc   2280
tttggaagcg agcgtccctt cagcgaagtt gtggcggatg ccaaggtcaa cggctacact   2340
gagcccgacc cccgtgatga cctgaacggc actgatgttg cccgcaaggt taccatccta   2400
acgcgagagt gcggcctaca actggagctg tctgacattc ccattgagtc tttggtgcct   2460
gaggcattgc gaggcttgaa ctcaagtgag gaatacatgg cacggctccc agaatttgat   2520
gcagagatgg ggcggcttgc tgcagaggca gaggcaagcg gggaagtcct tcgatacgtg   2580
ggcactgttg atgtgcagaa caaaactggc agcgtgggat taaaacagta ccccagaaac   2640
catgcattcg cacagctaga aggatctgac aacatcattt cctttcagac ctctcgttac   2700
aagaggcaac cgctcttcat ccgagggcct ggtgccggag ctgatgtgac ggctggtggc   2760
gtgttctctg acctcttgaa gctggctgct tacctgggtg caccctcttg a            2811
```

<210> SEQ ID NO 5
<211> LENGTH: 342
<212> TYPE: DNA
<213> ORGANISM: Dunaliella salina

<400> SEQUENCE: 5

```
atggctgggc tcaactttcc catcgaaact gcagtgcaag agatgcccag tgatggcagg     60
gacacgcttt catctgccct ggagcacatg caagtcaggg acagcctaaa aatgtacaac    120
```

```
aacttggtgg agcgttgctt ccgggagtgc agcgaggaca tgcgcagcaa agcgctgagt      180
tccaaggagg agcagtgtgt ggtcaagtgc tgcgagaagt ttatgaatgt gacagggcgt      240
gtgggcatgc gtttctctga attcttttca caaatggagg cagcagccca gcagcatatg      300
gcggagatgc tcaagcagca ggagcagcag agcaaatcat ag                          342
```

<210> SEQ ID NO 6
<211> LENGTH: 324
<212> TYPE: PRT
<213> ORGANISM: Dunaliella salina

<400> SEQUENCE: 6

```
Met Arg Pro Tyr Leu Leu Lys Gly His Asp Arg Pro Leu Thr Gln Val
1               5                   10                  15

Lys Phe Asn Arg Glu Gly Asp Leu Phe Val Thr Cys Ala Lys Asn Asn
            20                  25                  30

Gln Ser Cys Leu Trp Trp Ser Asp Asp Gly Lys Arg Val Gly Thr Phe
        35                  40                  45

Glu Gly His Asn Gly Ala Val Trp Ser Cys Asp Met Thr Trp Glu Ser
    50                  55                  60

Asp Arg Leu Ile Thr Ala Ser Ala Asp Gln Thr Val Arg Ile Trp Asp
65                  70                  75                  80

Met Thr Asn Gly Lys Glu Gln Phe Gln Phe Lys Met Gly Glu Pro Cys
                85                  90                  95

Arg Ala Cys Asn Leu Ser Leu Gly Glu Gln Met Leu Ala Phe Thr Thr
            100                 105                 110

Asp Ala Phe Met Gly Ser Ser Pro Met Val His Leu Ala Lys Leu Glu
        115                 120                 125

Asp Asp Leu Ser Gln Gln Thr Thr Lys Thr Val Leu Gly Ile Gln Ala
    130                 135                 140

Pro Lys Gly Arg Ile Thr Arg Val Phe Trp Ser Asp Met Asn Arg Thr
145                 150                 155                 160

Leu Val Thr Ser His Asp Gly Gly Phe Met Arg Lys Trp Asp Ser Glu
                165                 170                 175

Thr Gly Lys Met Leu Leu Glu Lys Gln Val His Glu Gly Asp Ile Gln
            180                 185                 190

Asp Met Gln Met Ser Pro Asp Gly Ala Tyr Phe Ile Thr Ala Ser Leu
        195                 200                 205

Asp Lys Thr Ala Lys Leu Val Asp Ala Val Gly Leu Glu Ala Leu Lys
    210                 215                 220

Thr Tyr Lys Thr Gly Arg Phe Val Gln Ser Ala Ala Ile Ser Pro Leu
225                 230                 235                 240

Phe Asp His Val Leu Leu Gly Gly Gln Asp Ala Ser Gln Val Thr
                245                 250                 255

Thr Thr Ser Ser Lys Ala Gly Gly Phe Glu Ala Arg Phe Phe His Lys
            260                 265                 270

Ile Tyr Gln Glu Glu Phe Gly Asn Val Arg Gly His Phe Gly Pro Ile
        275                 280                 285

Asn Thr Val Ala Phe His Pro Ser Gly Lys Ser Phe Leu Thr Gly Gly
    290                 295                 300

Glu Asp Gly Tyr Val Arg Leu His His Phe Asp Leu Asp Tyr Phe Thr
305                 310                 315                 320

Thr Lys Phe Phe
```

-continued

```
<210> SEQ ID NO 7
<211> LENGTH: 356
<212> TYPE: PRT
<213> ORGANISM: Dunaliella salina

<400> SEQUENCE: 7

Met Ala Cys Lys Ala Gln Thr Val Leu Phe Lys Glu Tyr Val Glu Val
1               5                   10                  15

Gly Glu Val Pro Pro Asp Asn Phe Gln Leu Arg Thr Ile Asp Leu Pro
            20                  25                  30

Ala Leu Lys Asp Gly Glu Val Leu Leu Glu Leu Gln Tyr Leu Ser Val
        35                  40                  45

Asp Pro Tyr Met Arg Gly Arg Met Arg Asn Ala Ala Gly Tyr Phe Val
    50                  55                  60

Gly Pro Phe Val Pro Gly Glu Ala Leu Ser Gly Gly Val Val Val
65                  70                  75                  80

Val Lys Glu Ser Lys Ala Pro Gly Ile Glu Lys Gly Lys Phe Tyr Ser
                85                  90                  95

Gly Met Val Pro Trp Thr Ser Pro Gln Ile Ala Thr Lys Ala Gln Met
            100                 105                 110

Glu Gln Met Gln Pro Val Asp Thr Asp Ile Leu Lys Leu Ala Lys Leu
        115                 120                 125

Pro Leu Ser Gly Tyr Ala Gly Val Phe Gly Leu Thr Gly Met Thr Ala
    130                 135                 140

Tyr Ala Ser Leu Thr Arg Ile Gly Lys Pro Lys Lys Gly Glu Thr Val
145                 150                 155                 160

Phe Val Ser Gly Ala Ala Gly Ala Val Gly Met Ile Val Gly Gln Met
                165                 170                 175

Cys Lys Asn Val Tyr Gly Cys Lys Val Val Gly Ser Ala Gly Ser Glu
            180                 185                 190

Asp Lys Val Glu Phe Leu Thr Lys Glu Leu Gly Phe Asp Ala Ala Trp
        195                 200                 205

Asn Tyr Lys Thr Met Pro Thr Leu Asp Ala Leu Asn Lys Phe Cys Pro
    210                 215                 220

Glu Gly Ile Asp Met Tyr Tyr Glu Asn Val Gly Gly Glu Gln Leu Glu
225                 230                 235                 240

Ala Ala Leu Glu Lys Cys Arg Glu Asn Ala Arg Ile Val Cys Cys Gly
                245                 250                 255

Met Ile Ser Gln Tyr Asn Lys Gly Asp Asp Arg Tyr Gly Val Lys
            260                 265                 270

Asn Leu Ala Asn Val Val Phe Lys Lys Ile Lys Met Glu Gly Phe Leu
        275                 280                 285

Leu Phe Gln Phe Leu Pro Glu Val Val Pro Glu Phe Phe Glu His Phe
    290                 295                 300

Pro Lys Trp Ile Ala Glu Gly Lys Ile Lys Asp Thr Glu Tyr Val Val
305                 310                 315                 320

Lys Gly Gly Leu Ala Asn Ala Gly Gln Ala Phe Cys Asp Met Met Ala
                325                 330                 335

Gly Lys Asn Lys Gly Lys Ala Val Val Lys Cys Val Asp Lys Asp Pro
            340                 345                 350

Ile Val Gly Asn
        355

<210> SEQ ID NO 8
<211> LENGTH: 347
<212> TYPE: PRT
```

<213> ORGANISM: Dunaliella salina

<400> SEQUENCE: 8

Met Ser Thr Ala Asn Val Gln Val Gln Gln Gly Asp Lys Pro Gln Pro
1               5                   10                  15

Val Lys Thr Gly Asn Thr Asn Glu Pro Asp Tyr Val Arg Leu Ser Asn
            20                  25                  30

Gly Val Leu Met Pro Leu Ile Gly Tyr Gly Thr Phe Gln Leu Gln Asp
        35                  40                  45

Ala Asp Met Val Lys Gln Ala Leu Glu Val Gly Tyr Arg His Leu Asp
    50                  55                  60

Cys Ala Ser Leu Tyr Gly Asn Gln Glu Leu Val Gly Arg Gly Ile Ala
65                  70                  75                  80

Ser Trp Ile Ala Ala Asp Pro Ser Lys Asn Lys Arg Glu Asp Leu Phe
                85                  90                  95

Val Thr Ser Lys Ile Phe Asn Asp Glu His Arg Pro Glu Leu Leu Arg
            100                 105                 110

Lys Ser Ala Glu Lys Ser Ile Ala Glu Leu Gly Thr Lys Tyr Leu Asp
        115                 120                 125

Leu Leu Leu Leu His Trp Pro Asn Ala Phe Lys Pro Gly Ser Gly Ser
    130                 135                 140

Ser Phe His Gly Asp Val Cys Pro Ala Glu Gly Glu Lys Pro Pro Gly
145                 150                 155                 160

Cys Val Val Phe Asp Asp Glu Val Thr His Glu Gln Thr Trp Arg Ala
                165                 170                 175

Met Glu Lys Leu Val Asp Asp Gly Leu Val Arg Cys Ile Gly Leu Ser
            180                 185                 190

Asn Phe Ser His Lys Glu Val Thr His Ile Cys Asn Ile Ala Arg Ile
        195                 200                 205

Lys Pro Thr Ile Asn Glu Ile Glu Leu His Pro Phe Leu Ala Gln Lys
    210                 215                 220

Glu Phe Val Ala Trp Cys Ala Ser Met Gly Val Thr Cys Leu Ala Tyr
225                 230                 235                 240

Gly Pro Leu Gly Gly Pro Asn Ala Tyr Leu Pro Asn Asp Leu Leu Pro
                245                 250                 255

His Pro Thr Val Thr Lys Val Ala Gln Glu Ala Gly Lys Thr Asn Gly
            260                 265                 270

Arg Ile Leu Val Lys Trp Ser Val Gln Arg Gly Val Pro Val Leu Val
        275                 280                 285

Lys Thr Gly Thr Ala Ser Arg Leu Lys Glu Asn Leu Trp Gly Met Met
    290                 295                 300

Asp Tyr Lys Leu Thr Asp Glu Gln Met Ala Ala Leu Asp Ser Leu Glu
305                 310                 315                 320

Asn Gly Lys Arg Leu Val Thr Val Pro Trp Lys Lys Trp Glu Thr Glu
                325                 330                 335

Pro Val Pro Asp Pro Val Pro Ser Thr Lys Ala
            340                 345

<210> SEQ ID NO 9
<211> LENGTH: 936
<212> TYPE: PRT
<213> ORGANISM: Dunaliella salina

<400> SEQUENCE: 9

Met Leu Leu Arg Ala Asn Cys Ala Ala Gly Leu Gly Cys Lys Ala Ser
1               5                   10                  15

-continued

```
Ser Gly Lys Thr Pro Ala Ala Ala Pro Ala Asn Val Ala Gly Phe Thr
             20                  25                  30
Ala Gln His Ser Ala Cys Phe Gly Lys Ala Ser Ser Ser Thr Arg Asn
         35                  40                  45
His His His Val Ile Thr Pro Leu Leu Pro Ser Cys Pro Ala Pro Leu
     50                  55                  60
Met Pro Gln Ala Ala His Ser Ser Ala Ile Cys Arg Ala Val Val Ala
 65                  70                  75                  80
Pro Val Glu Thr Glu Ala Gly Ala Pro Phe Gln Arg Gly Ser Gly
                 85                  90                  95
Trp Ala Leu His Lys Phe Gly Thr Cys Met Ala Ala Glu Arg
                100                 105                 110
Ile Ala Gly Ala Ser Lys Leu Met Ile Asp Ile Asn Pro Asp Ala Glu
                115                 120                 125
Gly Lys Val Ala Val Ser Ala Met Gly Ser His Pro Thr Ser Pro
    130                 135                 140
Leu Lys Val Thr Asp Val Ile Leu Gln Met Ile Ala Lys Ala Glu Arg
145                 150                 155                 160
Gln Asp Gln Arg Phe Leu Leu Asp Leu Ala Pro Gln Asp Lys His
                165                 170                 175
Val Asp Ser Ala Lys Glu Leu Leu Gly Glu Ser Lys Glu Leu Thr Tyr
            180                 185                 190
Phe Val Gly Arg Leu Leu Glu Asp Ile Asn Asn Leu Lys Ala Met Leu
        195                 200                 205
Asn Ala Met Ser Ile Ala Gly Met Thr Thr Glu Ala Phe Ser Asp Tyr
    210                 215                 220
Val Val Gly His Gly Glu Leu Trp Ser Ala Gln Leu Met Ala Leu Tyr
225                 230                 235                 240
Cys Gln Gln Leu Gly Ala Asp Cys Val Phe Met Asp Ala Arg Asp Val
                245                 250                 255
Leu Val Val Ser Pro Thr Ser Asp Gly Thr Ser Val Asp Leu Val Glu
            260                 265                 270
Asp Ala Ser Asn Ala Arg Leu Asp Ala Trp Phe Arg Lys His Gly Ser
        275                 280                 285
His Lys Leu Ile Ile Ala Thr Gly Phe Ile Ala Lys Asn Val Glu Gly
    290                 295                 300
Lys Ile Thr Thr Leu Lys Arg Asn Gly Ser Asp Leu Ser Ala Thr Thr
305                 310                 315                 320
Leu Gly Ala Leu Phe Arg Cys Gly His Ile Ser Ile Trp Thr Asp Val
                325                 330                 335
Asp Gly Val Tyr Ser Ala Asp Pro Arg Lys Val Pro Glu Ala Val Cys
            340                 345                 350
Leu Pro Ser Met Thr Tyr His Glu Ala Trp Glu Met Ser Tyr Phe Gly
        355                 360                 365
Ala Asn Val Leu His Pro Arg Thr Thr Leu Pro Ala Met Lys Tyr Asn
    370                 375                 380
Ile Pro Ile Thr Ile Arg Asn Phe Phe Arg Leu Glu Ala Pro Gly Thr
385                 390                 395                 400
Arg Val Ser Asp Val Ser Asp Ser Gln Ala Tyr Gly Gly His Asp
                405                 410                 415
Pro Thr Val Lys Gly Phe Ala Thr Ile Asp Asn Val Ser Leu Ile Ser
            420                 425                 430
Ile Glu Gly Thr Gly Met Val Gly Val Pro Gly Ile Ala Ser Thr Ile
```

-continued

```
               435                 440                 445
Phe Phe Thr Val Arg Asp Ala Asn Ile Asn Val Ile Met Ile Ser Gln
450                 455                 460

Ala Ser Ser Glu Gln Ser Ile Cys Phe Ala Val Lys Gln Ala Asp Gly
465                 470                 475                 480

Pro Ala Ala Val Arg Ala Leu Ser Arg Arg Phe Ala Glu Ser Ile Asn
                485                 490                 495

Ala Gly Arg Val Ser Lys Val Glu Ala Ile Glu Gly Cys Cys Val Leu
                500                 505                 510

Ala Ala Val Gly Gln Gly Met Val Asn Thr Lys Gly Val Ser Ala Thr
                515                 520                 525

Met Met Gly Ala Leu Ala Lys Ala Asn Val Asn Ile Lys Ala Ile Ala
530                 535                 540

Gln Gly Ser Ser Glu Tyr Asn Ile Thr Val Leu Val Asp Gln Lys Asp
545                 550                 555                 560

Ser Glu Arg Ala Leu Arg Ala Val His Ser Arg Phe Tyr Leu Ser Ala
                565                 570                 575

Thr Pro Leu Gly Ile Gly Leu Ile Gly Pro Gly Leu Ile Gly Gly Ala
                580                 585                 590

Leu Leu Gly Gln Ile Arg Asp Gln Ala Glu Thr Leu Arg Lys Asp Phe
                595                 600                 605

Ala Ile Asp Leu Arg Val Leu Gly Ile Ala Ser Ser Lys Thr Met Leu
610                 615                 620

Leu Gln Glu Lys Gly Val Asp Leu Glu Asn Trp Arg Glu Glu Phe Gln
625                 630                 635                 640

Gln Arg Gly Arg Pro Val Asp Leu Lys Ala Phe Ser Ser Ala Leu Ala
                645                 650                 655

Thr Ser Tyr Ile Pro Asn Cys Val Ile Asp Cys Thr Ala Ser Asp
                660                 665                 670

Ala Pro Pro Ala Ser Tyr Leu Glu Trp Met Lys Gln Gly Ile His Val
                675                 680                 685

Val Thr Pro Asn Lys Lys Leu Gly Ser Gly Pro Leu Ala Gln Tyr Gln
690                 695                 700

Asp Ile Lys Gln Val Gly Arg Asn Ser Tyr Thr His Phe Phe Tyr Glu
705                 710                 715                 720

Gly Thr Val Gly Ala Gly Leu Pro Val Ile Gly Thr Leu Lys His Leu
                725                 730                 735

Val Glu Thr Gly Asp Lys Val Glu Lys Val Glu Gly Ile Phe Ser Gly
                740                 745                 750

Thr Leu Ser Tyr Ile Phe Asn Thr Phe Gly Ser Glu Arg Pro Phe Ser
                755                 760                 765

Glu Val Val Ala Asp Ala Lys Val Asn Gly Tyr Thr Glu Pro Asp Pro
                770                 775                 780

Arg Asp Asp Leu Asn Gly Thr Asp Val Ala Arg Lys Val Thr Ile Leu
785                 790                 795                 800

Thr Arg Glu Cys Gly Leu Gln Leu Glu Leu Ser Asp Ile Pro Ile Glu
                805                 810                 815

Ser Leu Val Pro Glu Ala Leu Arg Gly Leu Asn Ser Ser Glu Glu Tyr
                820                 825                 830

Met Ala Arg Leu Pro Glu Phe Asp Ala Glu Met Gly Arg Leu Ala Ala
                835                 840                 845

Glu Ala Glu Ala Ser Gly Glu Val Leu Arg Tyr Val Gly Thr Val Asp
                850                 855                 860
```

-continued

Val Gln Asn Lys Thr Gly Ser Val Gly Leu Lys Gln Tyr Pro Arg Asn
865                 870                 875                 880

His Ala Phe Ala Gln Leu Glu Gly Ser Asp Asn Ile Ile Ser Phe Gln
            885                 890                 895

Thr Ser Arg Tyr Lys Arg Gln Pro Leu Phe Ile Arg Gly Pro Gly Ala
        900                 905                 910

Gly Ala Asp Val Thr Ala Gly Gly Val Phe Ser Asp Leu Leu Lys Leu
            915                 920                 925

Ala Ala Tyr Leu Gly Ala Pro Ser
        930                 935

<210> SEQ ID NO 10
<211> LENGTH: 113
<212> TYPE: PRT
<213> ORGANISM: Dunaliella salina

<400> SEQUENCE: 10

Met Ala Gly Leu Asn Phe Pro Ile Glu Thr Ala Val Gln Glu Met Pro
1               5                   10                  15

Ser Asp Gly Arg Asp Thr Leu Ser Ser Ala Leu Glu His Met Gln Val
            20                  25                  30

Arg Asp Ser Leu Lys Met Tyr Asn Asn Leu Val Glu Arg Cys Phe Arg
        35                  40                  45

Glu Cys Ser Glu Asp Met Arg Ser Lys Ala Leu Ser Ser Lys Glu Glu
    50                  55                  60

Gln Cys Val Val Lys Cys Cys Glu Lys Phe Met Asn Val Thr Gly Arg
65                  70                  75                  80

Val Gly Met Arg Phe Ser Glu Phe Phe Ser Gln Met Glu Ala Ala Ala
            85                  90                  95

Gln Gln His Met Ala Glu Met Leu Lys Gln Gln Glu Gln Gln Ser Lys
            100                 105                 110

Ser

<210> SEQ ID NO 11
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 11
aagcagtggt atcaacgcag agtacgcggg                              30

<210> SEQ ID NO 12
<211> LENGTH: 45
<212> TYPE: DNA
<213> ORGANISM: Artificial Sequence
<220> FEATURE:
<223> OTHER INFORMATION: Synthetic primer

<400> SEQUENCE: 12
ctaatacgac tcactatagg gcaagcagtg gtatcaacgc agagt             45

<210> SEQ ID NO 13
<211> LENGTH: 22
<212> TYPE: DNA
<213> ORGANISM: Artificial Sequence
<220> FEATURE:
<223> OTHER INFORMATION: Synthetic primer

<400> SEQUENCE: 13

-continued

```
ctaatacgac tcactatagg gc                                                    22

<210> SEQ ID NO 14
<211> LENGTH: 27
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (26)..(26)
<223> OTHER INFORMATION: n = A, C, G, or T
<220> FEATURE:
<221> NAME/KEY: misc_feature
<222> LOCATION: (27)..(27)
<223> OTHER INFORMATION: n = A, G, or C

<400> SEQUENCE: 14
tttttttttt tttttttttt tttttnn                                               27
```